United States Patent [19]

Collington et al.

[11] 4,410,521

[45] Oct. 18, 1983

[54] AMINOCYCLOPENTANE ESTERS AND PHARMACEUTICAL FORMULATIONS

[75] Inventors: Eric W. Collington, Welwyn; Peter Hallett, Bassingbourn; Christopher J. Wallis, Royston; Norman F. Hayes, Hitchin; John Bradshaw; Malcolm Carter, both of Ware, all of England

[73] Assignee: Glaxo Group Limited, England

[21] Appl. No.: 418,975

[22] Filed: Sep. 16, 1982

[30] Foreign Application Priority Data

Sep. 16, 1981 [GB] United Kingdom ............... 8127982
May 6, 1982 [GB] United Kingdom ............... 8213069

[51] Int. Cl.³ ................. A61K 31/55; A61K 31/535; C07D 295/14
[52] U.S. Cl. ................................. 424/244; 424/246; 424/248.5; 424/248.51; 424/248.54; 424/248.55; 424/250; 424/263; 424/267; 424/274; 424/45; 544/58.1; 544/58.2; 546/187; 546/191; 544/58.5; 546/205; 546/208; 544/55.6; 546/213; 546/214; 544/58.7; 546/230; 546/233; 544/171; 546/234; 546/235; 544/82; 546/238; 546/239; 544/85; 546/281; 548/517; 544/169; 548/523; 548/527; 544/87; 548/567; 548/568; 544/121; 548/569; 548/573; 544/130; 542/426; 260/239 BF; 544/131; 260/243.3; 260/244.4; 544/141; 260/245.7; 260/330.3; 544/146; 260/330.6; 260/330.9; 544/152; 544/400; 544/399; 544/158; 544/396; 544/379; 544/159; 544/374; 544/372; 544/162; 544/364; 544/360; 544/163; 544/357; 544/172; 544/165; 544/167

[58] Field of Search .............. 544/58.1, 58.2, 58.5, 544/58.6, 58.7.82, 85, 87, 121, 130, 131, 141, 146, 152, 158, 159, 163, 165, 162, 169, 171, 172, 167, 357, 360, 364, 372, 374, 379, 396, 399, 400; 546/187, 191, 205, 208, 213, 214, 230, 233, 234, 235, 238, 239, 281; 548/523, 527, 567, 568, 517, 567, 569, 573; 260/239 BF, 243.3, 244.4, 245.7, 330.3, 330.6, 370.9; 542/426; 424/244, 246, 258.5.248.51, 248.54, 248.55, 250, 267, 263, 274, 45

[56] References Cited

U.S. PATENT DOCUMENTS 4,265,891 5/1981 Collington et al. ............ 424/244
4,342,756 8/1982 Collington et al. ............ 546/238

Primary Examiner—Robert W. Ramsuer
Attorney, Agent, or Firm—Bernard, Rothwell & Brown

[57] ABSTRACT

Compounds are described of the formula

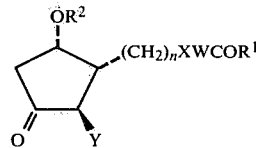

in which
—COR$^1$ is a complex ester or thioester group,
W is alkylene,
X is cis or trans —CH=CH or —CH$_2$CH$_2$—,
n is 1 or 2,
Y is a saturated heterocyclic amino group having 5–8 ring members, and
R$^2$ is unsubstituted or substituted phenylalkyl, thienylalkyl, naphthylalkyl or cinnamyl,
and their salts and solvates.

These compounds inhibit blood platelet aggregation and bronchoconstruction and may be formulated for use as antithrombotic and antiasthmatic agents.

9 Claims, No Drawings

AMINOCYCLOPENTANE ESTERS AND PHARMACEUTICAL FORMULATIONS

British Pat. Nos. 2,028,805, 2,070,591 and 2,075,503 referred to below correspond to Collington et al U.S. Pat. No. 4,265,891, applications Ser. Nos. 223,315 and 223,316 (both filed on Jan. 8, 1981), U.S. Pat. Nos. 4,342,756 and 4,327,092, incorporated herein by reference.

The endoperoxides prostaglandins $G_2$ and $H_2$ and thromboxane $A_2$ are naturally occurring reactive metabolites of arachidonic acid in human platelets. They are not only potent aggregatory agents but are also constrictors of vascular and bronchial smooth muscle, and therefore substances which antagonise their effects are of considerable interest in human medicine.

We have now found a new group of compounds which have shown endoperoxide and thromboxane antagonist activity, and are therefore of interest in the treatment of asthma and cardiovascular diseases.

The invention thus provides compounds of the general formula (1)

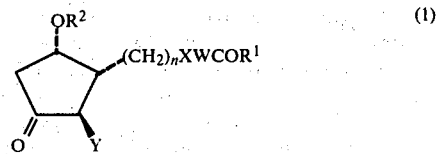

wherein $R^1$ is (a) —$AR^3$ where A is —O— or —S— and $R^3$ is phenyl [optionally substituted by $C_{1-4}$ alkyl (e.g. methyl, ethyl or t-butyl), $C_{1-4}$ alkoxy, (e.g. methoxy, ethoxy or butoxy), $C_{1-4}$ alkanoyl (e.g. acetyl), methylthio, methylsulphinyl, methylsulphonyl, halogen (e.g. chlorine or bromine), —$CO_2R^4$ [where $R^4$ is a hydrogen atom or $C_{1-4}$ alkyl (e.g. methyl or ethyl) or phenyl], —$NHCOR^4$ (e.g. acetamido), —$CONR^5R^6$ [where $R^5$ and $R^6$ may be the same or different and are each a hydrogen atom or $C_{1-4}$ alkyl (e.g. methyl or ethyl)], $C_{1-4}$ alkylsulphonylamino (e.g. $CH_3SO_2NH$— or $C_2H_5SO_2NH$—), formyl, nitro, cyano, phenyl or —$NR^5R^6$ (e.g. amino, dimethylamino or diethylamino)];

(b) —$OCH_2COR^7$ wherein $R^7$ is phenyl [optionally substituted by a halogen atom (e.g. Cl or Br), $C_{1-4}$ alkyl (e.g. methyl, ethyl or t-butyl) or $C_{1-4}$ alkoxy, (e.g. methoxy, ethoxy or butoxy)] or —$NH_2$;

(c) —$A(CH_2)_mBR^5$ where m is 1–3 and B is —O— or —S—, provided that when m is 1, $R^5$ is not a hydrogen atom (e.g. $CH_3OCH_2O$—, $CH_3CH_2OCH_2O$—, $CH_3SCH_2O$— or $HOC_2H_4O$—);

(d) —$A(CH_2)_pR^8$ where p is 2 or 3 and $R^8$ is an N-attached $C_{1-4}$ dialkylamino (e.g. dimethyl- or diethyl-amino), morpholino, piperidino, pyrrolidino, acetylamino or benzoylamino group;

(e) —$OCH(CH_2N(CH_3)_2)_2$;

(f)

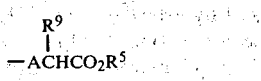

where $R^9$ is a hydrogen atom, methyl or phenyl; examples of suitable $R^5$ groups being methyl and ethyl;

(g) —$OCH_2OCOR^{10}$ where $R^{10}$ is $C_{1-4}$ alkyl (e.g. methyl or ethyl), methoxy or phenyl;

(h) —$OCH_2SCOR^{11}$ wherein $R^{11}$ is $C_{1-4}$ alkyl (e.g. methyl or ethyl);

(i) pyridinyloxy or pyridinylthio;

(j) 1-(acetyloxy)ethoxy, (acetyloxy)phenylmethoxy, tetrahydro-5-oxo-2-furanyloxy, tetrahydro-2-oxo-3-furanyloxy, triphenylmethoxy or diphenylmethoxy; or (k) —$OR^{12}$ where $R^{12}$ is $C_{3-6}$ alkenyl (e.g. propenyl or butenyl), $C_{5-7}$ cycloalkyl (e.g. cyclopentyl, cyclohexyl or cycloheptyl) optionally substituted by one or more $C_{1-4}$ alkyl (e.g. methyl, ethyl or t-butyl) groups, —$CH_2CCl_3$ or furanylmethyl;

n is 1 or 2;

W is straight or branched $C_{1-7}$ alkylene;

X is cis or trans —CH=CH— or —$CH_2CH_2$—;

Y is a saturated heterocyclic amino group (attached to the cyclopentane ring via the nitrogen atom) which has 5–8 ring members and (a) optionally contains in the ring —O—, —S—, —$SO_2$—, or $NR^{13}$ (where $R^{13}$ is a hydrogen atom, $C_{1-7}$ alkyl or aralkyl having a $C_{1-4}$ alkyl portion); and/or (b) is optionally substituted by one or more $C_{1-4}$ alkyl groups;

$R^2$ is (i) straight or branched $C_{1-5}$ alkyl substituted by (a) phenyl [optionally substituted by $C_{1-6}$ alkyl, $C_{5-7}$ cycloalkyl, phenylalkyl having a $C_{1-3}$ alkyl portion, thienyl, phenyl (optionally substituted by $C_{1-4}$ alkyl, $C_{1-4}$ alkoxy or phenyl), benzoyl (optionally substituted by $C_{1-4}$ alkyl, $C_{1-4}$ alkoxy, halogen, trifluoromethyl or phenyl) or $C_{5-7}$ cycloalkanoyl], (b) thienyl [optionally substituted by $C_{5-7}$ cycloalkyl or phenyl (optionally substituted by $C_{1-3}$ alkyl, $C_{1-3}$ alkoxy or halogen)], or (c) naphthyl (optionally substituted by $C_{1-4}$ alkyl or $C_{1-4}$ alkoxy), or (ii) cinnamyl (optionally substituted by benzoyl); and the physiologically acceptable salts and solvates thereof.

The structural formulae herein are to be understood to include the enantiomers of each of the compounds concerned as well as mixtures of the enantiomers including racemates, even though the precise structure as set out only relates to one enantiomer.

The amino group Y enables the compounds to form salts with inorganic or organic acids, e.g. hydrochlorides or maleates. Also, when the group $R^1$ contains a —COOH group, salts may be formed with bases. Examples of such salts are alkali metal (e.g. sodium), alkaline earth metal (e.g. calcium) and amine (e.g. piperazine) salts.

The heterocyclic amino group Y may for example have a 5, 6 or 7-membered ring, e.g. pyrrolidino, piperidino, morpholino, piperazino, thiomorpholino, 1,1-dioxothiomorpholino, homomorpholino and hexamethyleneimino. Examples of the optional substituents which may be present on a second nitrogen atom in the ring are methyl, ethyl and benzyl. The carbon atoms of the heterocyclic rings may for example be substituted by methyl or ethyl. Y is preferably a morpholino or piperidino group.

In the group —$(CH_2)_nXWCOR^1$, n is preferably 2. X is preferably a cis —CH=CH— group. The W group may for example contain 1–5 carbon atoms in a straight or branched chain and is preferably —$CH_2CH_2CH_2$— when n is 1, and —$CH_2CH_2$— or —$CH_2CH_2CH_2CH_2$— when n is 2.

In the $R^1$ groups, A (where present) is preferably —O—. In $R^1$ groups of the type (a), $R^3$ is preferably phenyl (optionally substituted by $C_{1-4}$ alkyl, $C_{1-4}$ alkoxy, $C_{1-4}$ alkanoyl, methylsulphonyl, —COOR$^4$ (where $R^4$ is a hydrogen atom or $C_{1-4}$ alkyl), —NHCOR$^4$ (where $R^4$ is $C_{1-4}$ alkyl) or —CONR$^5$R$^6$). In $R^1$ groups, of the type (b), $R^7$ is preferably —NH$_2$, phenyl or halophenyl. In $R^1$ groups of the type (c), m is preferably 1 or 2 and $R^5$ is preferably $C_{1-4}$ alkyl. In $R^1$ groups of the type (d), $R^8$ is preferably $C_{1-4}$ dialkylamino, morpholino or acetylamino. In $R^1$ groups of the type (f), $R^9$ is preferably methyl and $R^5$ is preferably $C_{1-4}$ alkyl.

Particularly preferred $R^1$ groups are —OCH$_2$OCOCH$_3$, —OCH$_2$SCH$_3$, —OCH$_2$CH$_2$CH$_2$NHCOCH$_3$, —OCH$_2$CONH$_2$, 4-acetamidophenoxy and allyloxy.

When $R^2$ is a substituted alkyl group, the alkylene portion may for example contain 1–3 carbon atoms (e.g. methylene, ethylene or propylene) and is preferably a methylene group.

In $R^2$ groups of the type (i) (a), the phenyl group may be substituted by, for example, methyl, ethyl, t-butyl, cyclohexyl, benzyl, phenethyl, phenyl (optionally substituted by methyl, ethyl, methoxy or butoxy), benzoyl (optionally substituted by methyl, ethyl, methoxy, butoxy, chlorine or bromine) or cyclohexanoyl groups.

In $R^2$ groups of the type (i) (b), the thienyl group may be substituted by, for example, methyl, ethyl, methoxy, ethoxy, cyclohexyl or phenyl (optionally substituted by methyl, ethyl, methoxy, ethoxy, chlorine or bromine) groups.

$R^2$ is preferably a benzyl group in which the phenyl group is substituted by thienyl or phenyl (which phenyl group may itself be optionally substituted by $C_{1-4}$ alkyl or $C_{1-4}$ alkoxy).

Particularly preferred $R^2$ groups are benzyl groups in which the phenyl portion is substituted (preferably in the para-position) by a phenyl, tolyl or methoxyphenyl substituent.

A particularly preferred group of compounds has the formula (1) in which:
$R^1$ is —OCH$_2$OCOCH$_3$, —OCH$_2$SCH$_3$, —OCH$_2$CH$_2$CH$_2$NHCOCH$_3$, —OCH$_2$CONH$_2$, 4-acetamidophenoxy, or allyloxy,
W is —CH$_2$CH$_2$—
n is 2
X is cis —CH=CH—,
Y is morpholino or piperidino and
$R^2$ is benzyl in which the phenyl group is substituted by phenyl, tolyl or methoxyphenyl and the physiologically acceptable salts and solvates thereof.

In general, the compounds of formula (1) in which the carbon atoms carrying the —(CH$_2$)$_n$XWCOR$^1$ group is in the R- configuration (and mixtures containing this isomer) are preferred.

Compounds of formula (1) inhibit blood platelet aggregation and bronchoconstriction. A test to determine inhibition of blood platelet aggregation is as described by G. V. Born in Nature 194, 927–929 (1962) except in that collagen is used instead of ADP as the proaggregatory agent. Alternatively, starved guinea-pigs are dosed orally with the compound to be tested in a suitable vehicle. Platelet rich plasma is prepared from each animal and aggregation to a range of collagen concentrations is measured after the method of Born (Nature 194, 927–929, (1962)). Collagen concentration-effect curves for each sample of plasma are calculated and results are expressed as the shift of the curves following treatment with the compound.

The ability of the compounds of the invention to inhibit bronchoconstriction is determined either in the anaesthetized guinea pig by measuring the effect of the compound to be tested on the dose response curve of the bronchoconstrictor [1R-[1α,4α,5β(Z),6α-(1E,3S*)]]-7-[6-(3-hydroxy-1-octenyl)-2-oxabicyclo[2,2,1]hept-5-yl]-5-heptenoic acid (U-46619), or by the test described by K. M. Lulich et al in *British Journal of Pharmacology* 58, 71–79 (1976) except guinea pig lung is used instead of cat lung.

The compounds are thus of interest in the treatment of asthma, and as inhibitors of platelet aggregation and thrombosis for use in renal dialysis and the treatment and prevention of occlusive vascular diseases such as arteriosclerosis, atherosclerosis, peripheral vascular disease, cerebral vascular disease including transient ischaemic attacks, stroke, pulmonary embolism, diabetic retinopathy, post operative thrombosis, angina and myocardial infarction. They may be formulated in conventional manner for use, with one or more pharmaceutical carriers.

For oral administration, the pharmaceutical composition may take the form of, for example, tablets, capsules, powders, solutions, syrups, or suspensions prepared by conventional means with acceptable excipients.

The compounds may be formulated for parenteral administration by bolus injections or continuous infusion. Formulations for injections may be presented in unit dosage form in ampoules, or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution before use with a suitable vehicle, e.g. sterile pyrogen-free water.

For administration by inhalation the compounds are conveniently delivered in the form of an aerosol spray presentation from pressurised packs or a nebuliser, or as a cartridge from which the powdered composition may be inhaled with the aid of a suitable device. In the case of a pressurised aerosol the dosage unit may be determined by providing a valve to deliver a metered amount.

For use as antithrombotic agents, the compounds are preferably administered orally, for example in amounts of 0.05 to 10 mg/kg body weight, 1 to 4 times daily.

For use in the treatment of asthma, the compounds may also be administered orally in amounts of 0.05 to 10 mg/kg body weight, 1 to 4 times daily; preferably however they are administered by inhalation at doses varying from 0.3 to 30 mg, 1 to 4 times daily. The compounds may be used in combination with other antiasthmatic agents.

The precise dose administered will of course depend on the age and condition of the patient.

Suitable methods for preparing the compounds of the invention are described below, the groups $R^1$, $R^2$, $R^3$, $R^5$, A, B, W, X and Y being as defined above except where otherwise indicated.

(a) The compounds of of the invention may be prepared by esterification of the corresponding carboxylic acid, i.e. a compound in which $R^1$ represents a hydroxyl group. Conventional esterification methods may be used.

For example, compounds in which $R^1$ is a group of the type a, c (other than those in which m is 1), d, e, f, and k may be prepared by treating a reactive derivative of the corresponding carboxylic acid with an appropriate alcohol or thiol $R^1H$. The reactions may for example be carried out at room temperature using a solvent such as a ketone (e.g. methylethyl ketone or acetone) or acetonitrile and, where appropriate, in the presence of pyridine.

The reactive derivative is conveniently a mixed anhydride of the acid, formed for example by treatment of the acid with a chloroformate in the presence of a suitable base, e.g. triethylamine or pyridine at $-10°$ C.

The chloroformate may for example be a $C_{1-6}$ alkyl (e.g. iso-butyl), aryl (e.g. phenyl) or aralkyl (e.g. benzyl) chloroformate.

The same group of esters may also be prepared by first reacting the corresponding carboxylic acid with dicyclohexylcarbodiimide in the presence of 4-pyrrolidinopyridine, and then treating the product with the alcohol or thiol $R^1H$. This reaction is conveniently performed at room temperature in a solvent such as ether or $CH_2Cl_2$.

Again for example, compounds in which $R^1$ is a group of the type b, c, d, f, g, h, or j and A (when present) is —O— may be prepared by reacting the corresponding carboxylic acid with an appropriate halide $R^{14}$Hal, where Hal represents halogen and $R^{14}$ is as just defined for $R^1$, excluding the terminal —O—. The reaction is carried out in the presence of a suitable base, e.g. potassium t-butoxide or potassium carbonate or a sterically hindered amine such as N,N-diisopropylethylamine, triethylamine or dicyclohexylamine in a suitable solvent (such as acetonitrile, dimethylformamide, $CH_2Cl_2$ or a ketone, e.g. methylethyl ketone or acetone), for example at a temperature from $0°$ C. to room temperature.

This latter reaction may also be used to prepare compounds in which $R^1$ is a group of type (c) in which A is —S— and m is 1, by reacting the corresponding thioacid (i.e. in which $R^1$ is —SH) with a halide $R^5BCH_2$—Hal. The thioacid starting material may be prepared in situ by treating a reactive derivative of the corresponding carboxylic acid (e.g. a mixed anhydride, as above) with a hydrosulphide (e.g. NaHS).

Compounds in which $R^1$ is a group of the type (f) where A is —O— may also be prepared by reacting the corresponding carboxylic acid with the appropriate diazoalkane in a solvent such as dioxane in the presence of a salt such as copper (II) chloride, for example at room temperature.

Compounds in which $R^1$ is a group of the type (i) where A is —S— may also be prepared by reacting the corresponding carboxylic acid with the appropriate pyridyldisulphide in the presence of triphenylphosphine in a solvent such as benzene, for example at room temperature.

Many of the carboxylic acids corresponding to the esters of formula (1) required as starting materials for process (a), i.e. compounds of formula (2)

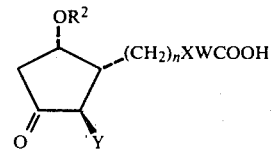

are described in British Pat. Specification Nos. 2,028,805A, 2,070,591A and 2,075,503A and those containing other $R^2$ groups may be prepared by the same general methods, using starting materials containing the desired $R^2$ group.

(b) The compounds of the invention may also be prepared by reduction of a corresponding compound in which X is an acetylene group. Suitable methods of reduction including using hydrogen in the presence of a catalyst, e.g. palladium on a support (e.g. $CaCO_3$ or $BaSO_4$) and poisoned for example by lead or quinoline. Suitable solvents include ethyl acetate and methanol. This reaction is particularly suitable for preparing compounds in which X is cis —CH=CH—.

The acetylenes required as starting materials may be prepared by first brominating (e.g. with bromine in $CH_2Cl_2$) a compound of formula (3)

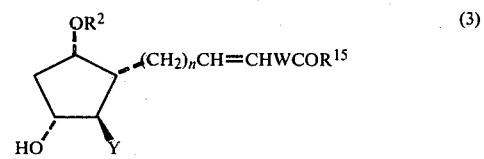

(where $R^{15}$ is $C_{1-6}$ alkoxy, e.g. methoxy) to give the corresponding compound in which X is —CHBr.CHBr—. The latter dibromo compound is then dehydrobrominated to form the acetylene group, for example in two stages, using potassium t-butoxide first at $0°$ C. and then at room temperature. Hydrolysis of the resulting acetylene ester to the corresponding acid ($R^1$=OH) using a base such as NaOH at e.g. room temperature, followed by oxidation of the ring hydroxy group (using e.g. chromic acid in acetone at a low temperature e.g. $-20°$ C. to room temperature) gives a corresponding acid of formula (1) in which X is an acetylene group and $R^1$ is —OH. Esterification of the acetylene acids as described in method (a) then gives the required acetylene ester starting materials. The starting materials of formula (3) may be prepared by the methods generally described in British Pat. Specification Nos. 2,028,805A, 2,070,591A and 2,075,503A.

(c) Compounds in which $R^1$ is a group of type (a) in which $R^3$ is phenyl substituted by amino may be prepared by reduction of the corresponding compound in which $R^3$ is phenyl substituted by azido. The reduction may for example be effected with zinc and potassium dihydrogen phosphate in a suitable solvent, e.g. tetrahydrofuran.

(d) Compounds in which X is —$CH_2CH_2$— may be prepared by catalytic hydrogenation of a corresponding compound in which X is —CH=CH—, using a catalyst such as palladium oxide. Alcohols such as ethanol are suitable solvents and the reaction may be performed at room temperature.

(e) Compounds of formula (1) may be prepared by oxidising a corresponding hydroxy compound, e.g. a compound of formula (4)

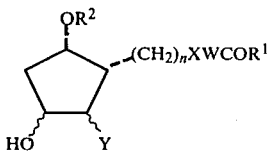

(4)

Suitable methods of oxidation including using a $Cr^{vl}$ oxidising reagent in a suitable solvent, e.g. chromic acid in acetone (e.g. Jones reagent, preferably used in the presence of a diatomaceous silica such as Celite) or $CrO_3$ in pyridine. These reagents are for example used at temperatures of $-20°$ C. to room temperature.

Other important methods include using an activated sulphur reagent, e.g. (i) N-chlorosuccinimide-dimethylsulphide complex in a suitable solvent (e.g. toluene or dichloromethane) at temperatures of for example $-25°$ to $25°$ C., preferably at $0°-5°$ C., (ii) a dialkylsulphoxide (e.g. dimethylsulphoxide) activated by a suitable electrophilic reagent (such as oxalyl chloride, acetyl bromide or thionyl chloride) in a suitable solvent (e.g. toluene or dichloromethane), e.g. at $-70°$ to $-20°$ C.; dicyclohexylcarbodiimide can also be used as the electrophilic reagent (preferably in the presence of $CF_3COOH$ or its pyridinium salt) at for example $-10°$ C. using the same solvents, or (iii) pyridine-$SO_3$ complex in dimethylsulphoxide, preferably at $0°$ C. to room temperature. When Y is in the α-configuration conditions should be chosen to effect epimerisation, either at the same time or after oxidation.

The esters of formula (4) may be prepared by esterification of the corresponding carboxylic acid in which $R^1$ is a hydroxyl group, for example using the methods described above in connection with process (a).

The carboxylic acid starting materials may be prepared by the methods generally described in British Pat. Specification Nos. 2,028,805A, 2,070,591A and 2,075,503A.

Compounds of formula (1) in which the ester group is sensitive to oxidation are preferably prepared by the esterification process (a).

(f) Compounds of formula (1) in which $R^1$ is $-OCH_2SCH_3$ may be prepared by simultaneous oxidation and esterification of the corresponding hydroxy carboxylic acid, i.e. a compound of formula (4) in which $R^1$ is $-OH$.

This reaction may be performed by treating the hydroxy carboxylic acid with dimethylsulphoxide in the presence of an electrophilic reagent, for example as described above for process (e), preferably using dicyclohexylcarbodiimide in the presence of pyridinium trifluoroacetate. The reaction is preferably carried out at room temperature.

(g) Where salts of compounds of formula (1) are desired such salts may be formed by conventional methods, for example by treatment with an acid or when $R^1$ contains a $-COOH$ group, with a base. Salts of acids may be prepared by adding the acid to a solution of the compound of formula (1) in an organic solvent such as ether. Salts of bases may be prepared by adding the base (e.g. an amine such as piperazine) in a solvent such as ether.

When a specific enantiomer of formula (1) is required, starting materials having the desired stereochemical configuration should be used in the above processes. Such starting materials may for example be prepared from an enantiomeric bromohydrin as generally described in British Patent Specification No. 2,075,503A. The following examples illustrate the invention.

'Jones reagent' is a solution of chromic acid and sulphuric acid in water. A 2.67 M solution contains $CrO_3$ (26.7 g) and concentrated $H_2SO_4$ (23 ml) made up to 100 ml with water.

Temperatures are in °C. The following abbreviations are used: 'Dried' refers to drying with $MgSO_4$; T.L.C.—thin layer chromatography using $SiO_2$; PE—petroleum ether (boiling at 40°-60° unless otherwise stated); THF—tetrahydrofuran; DMF—dimethylformamide; ER—ether; EA—ethyl acetate; DMSO—dimethylsulphoxide; IPA—isopropyl alcohol. Chromatography was carried out using silica gel unless otherwise stated. The following abbreviations define the eluent used for the chromatography and T.L.C.

(A) 19:1 EA-$CH_2Cl_2$
(B) 9:1 ER-methanol
(C) ER
(D) 92:8 EA-methanol
(E) EA
(F) 9:1 EA-methanol
(G) 19:1 ER-methanol
(H) 4:1 ER-PE (b.p. 60°-80°)
(I) 49:1 ER-methanol
(J) 2:1 ER-PE (b.p. 60°-80°)
(K) 2:1 ER-PE
(L) 1:1 ER-PE (b.p. 60°-80°)
(M) 3:1 ER-PE
(N) 4:1 ER-PE
(O) 4:1 ER-methanol
(P) 39:1 ER-methanol
(Q) 3:1 EA-PE
(R) 94:5:1 ER-methanol-$Et_3N$
(S) 1:1 ER-PE
(T) 7:3 ER-isopentane
(U) 65:35 ER-PE (b.p. 60°-80°)
(V) 7:3 ER-PE (b.p. 60°-80°)
(W) 9:1 ER-PE (b.p. 60°-80°)
(X) 4:1 PE (b.p. 60°-80°)-EA
(Y) 75:24:1 ER-PE-$CH_2Cl_2$
(Z) 3:1 ER-$CH_2Cl_2$
(AA) 5:4 PE (b.p. 60°-80°):ER
(BB) 13:9 EA-PE (b.p. 60°-80°)
(CC) 3:1 ER-PE (b.p. 60°-80°)
(DD) 13:7 PE (b.p. 60°-80°)-EA
(EE) 7:3 ER-PE
(FF) 4:1 EA-methanol
(GG) 24:1 ER-methanol
(HH) 21:4 ER-methanol
(II) 4:1 EA-PE (b.p. 60°-80°)
(JJ) 3:1 ER-isopentane
(KK) 13:7 ER-PE (b.p. 60°-80°)

The preparation of Intermediates 1–20 is described in British Patent Specification No. 2,075,503A.

Intermediate 1

[1α(Z),2β,5α]-(±)-7-[5-[[(1,1'-Biphenyl)-4-yl]methoxy]-2-(4-morpholinyl)-3-oxocyclopentyl]-4-heptenoic acid.

Intermediate 2

[1α(Z),2β,5α]-(±)-7-[5-[[4'-Methoxy(1,1'-biphenyl)-4-yl]methoxy]-3-oxo-2-(4-thiomorpholinyl)cyclopentyl]-4-heptenoic acid, S-dioxide.

Intermediate 3

[1α(Z),2β,5α]-(±)-7-[2-(4-Morpholinyl)-3-oxo-5-[4-(phenylmethyl)phenylmethoxy]cyclopentyl]-4-heptenoic acid, compound with piperazine (2:1).

Intermediate 4

[1α(Z),2β,5α(E)]-(±)-7-[2-(4-Morpholinyl)-3-oxo-5-[(3-phenyl-2-propenyl)oxy]cyclopentyl]-4-heptenoic acid.

Intermediate 5

[1α(Z),2β,5α]-(±)-7-[5-[[(1,1'-Biphenyl)-4-yl]methoxy]-3-oxo-2-(4-thiomorpholinyl)cyclopentyl]-4-heptenoic acid.

Intermediate 6

[1α(Z),2β,3α,5α]-(±)-7-[3-Hydroxy-5-[[4'-methoxy(1,1'-biphenyl)-4-yl]methoxy]-2-(4-morpholinyl)cyclopentyl]-4-heptenoic acid.

Intermediate 7

[1α(Z),2β,3α,5α]-(±)-7-[3-Hydroxy-5-[[4'-methyl(1,1'-biphenyl)-4-yl]methoxy]-2-(4-morpholinyl)cyclopentyl]-4-heptenoic acid.

Intermediate 8

[1α(Z),2β,3α,5α(E)]-(±)-7-[3-Hydroxy-2-(4-morpholinyl)-5-[(3-phenyl-2-propenyl)oxy]cyclopentyl]-4-heptenoic acid.

Intermediate 9

[1α(Z),2β,3α,5α]-(±)-7-[5[[(1,1'-Biphenyl)-4-yl]methoxy]-3-hydroxy-2-(1-piperidinyl)cyclopentyl]-4-heptenoic acid.

Intermediate 10

[1R-[1α(Z),2β,5α]]-(−)-7-[5-[[(1,1'-Biphenyl)-4-yl]methoxy]-2-(4-morpholinyl)-3-oxocyclopentyl]-4-heptenoic acid.

Intermediate 11

[1α(Z),2β,3α,5α]-(±)-7-[5-[3-[(1,1'-Biphenyl)-4-yl]propoxy]-3-hydroxy-2-(4-morpholinyl)cyclopentyl]-4-heptenoic acid.

Intermediate 12

[1α(Z),2β,3α,5α]-(±)-9-[5-[[(1,1'-Biphenyl)-4-yl]methoxy]-3-hydroxy-2-(4-morpholinyl)cyclopentyl]-6-nonenoic acid.

Intermediate 13

[1α(Z),2β,3α,5α]-(±)-7-[3-Hydroxy-5-[[3'-methoxy(1,1'-biphenyl)-4-yl]methoxy]-2-(4-morpholinyl)cyclopentyl]-4-heptenoic acid.

Intermediate 14

[1α(Z),2β,3α,5α]-(±)-7-[3-Hydroxy-2-(4-morpholinyl)-5-[(2-phenylthien-4-yl)methoxy]cyclopentyl]-4-heptenoic acid.

Intermediate 15

[1α(Z),2β,3α,5α]-(±)-7-[3-Hydroxy-5-[[4'-methyl(1,1'-biphenyl)-4-yl]methoxy]-2-(4-thiomorpholinyl)cyclopentyl]-4-heptenoic acid, S-dioxide.

Intermediate 16

[1α(Z),2β,3α,5α]-(±)-7-[3-Hydroxy-2-(4-morpholinyl)-5-[4-(thien-2-yl)phenylmethoxy]cyclopentyl]-4-heptenoic acid.

Intermediate 17

[1α(Z),2β,3α,5α]-(±)-7-[3-Hydroxy-2-(4-morpholinyl)-5-(2-naphthalenylmethoxy)cyclopentyl]-4-heptenoic acid.

Intermediate 18

[1α(Z),2α,3α,5α]-(±)-7-[5-[[(1,1'-Biphenyl)-4-yl]methoxy]-3-hydroxy-2-(4-morpholinyl)cyclopentyl]-4-heptenoic acid.

Intermediate 19

[1α(Z),2β,3β,5α]-(±)-7-[5-[[(1,1'-Biphenyl)-4-yl]methoxy]-3-hydroxy-2-(4-morpholinyl)cyclopentyl]-4-heptenoic acid.

Intermediate 20

(1α,2β,5α)-(±)-7-[5-[[(1,1'-Biphenyl)-4-yl]methoxy]-2-(4-morpholinyl)-3-oxocyclopentyl]-4-heptynoic acid.

Intermediate 21(a)

[1α(Z),2α,3α,5α]-(±)-(Acetyloxy)methyl 7-[5-[[(1,1'-Biphenyl)-4-yl]methoxy]-3-hydroxy-2-(4-morpholinyl)cyclopentyl]-4-heptenoate, m.p. 69°–71° from Intermediate 18 by the procedure described for the preparation of Example 3a (Method 1). Purification by chromatography (A). I.R. (CHBr$_3$) 3480, 1760 cm$^{-1}$.

The following compounds were prepared by a similar procedure:

(b) (1α,2β,5α)-(±)-(Acetyloxy)methyl 7-[5-[[(1,1'-Biphenyl)-4-yl]methoxy]-2-(4-morpholinyl)-3-oxocyclopentyl]-4-heptynoate, from Intermediate 20. Purification by chromatography (C) gave the title compound as an oil. I.R. (Neat) 1760, 1740 cm$^{-1}$.

(c) [1α(Z),2β,3α,5α]-(±)-(Acetyloxy)methyl 7-[3-Hydroxy-2-(4-morpholinyl)-5-[4-(thien-2-yl)phenylmethoxy]cyclopentyl]-4-heptenoate, from Intermediate 16. Purification by chromatography (F) gave the title compound as an oil. I.R. (Neat) 3430, 1765 cm$^{-1}$.

Intermediate 22

[1α(Z),2β,3α,5α]-(±)-Methoxymethyl 7-[5-[3-[(1,1'-Biphenyl)-4-yl]propoxy]-3-hydroxy-2-(4-morpholinyl)cyclopentyl]-4-heptenoate Chloromethylmethyl ether (0.008 ml) was added to a mixture of Intermediate 11 (0.05 g) and dicyclohexylamine (0.02 ml) in dry DMF (0.75 ml). After 10 min saturated NH$_4$Cl solution (10 ml) was added and the suspension extracted with EA (3×20 ml). The combined extracts were dried, filtered and evaporated to afford the title compound as an oil (0.042 g). I.R. (Neat) 3400, 1740 cm$^{-1}$.

Intermediate 23

[1α(Z),2β,3α,5α]-(±)-(Methylthio)methyl 9-[5-[[(1,1'-Biphenyl)-4-yl]methoxy]-3-hydroxy-2-(4-morpholinyl)cyclopentyl]-6-nonenoate From Intermediate 12 (1.25 g), chloromethyl methyl sulphide (0.61 ml) and diisopropylethylamine (1.5 ml) according to the method described for the preparation of Intermediate 22. Purification by chromatography (D)

gave the title compound as an oil (0.37 g). I.R. (CHBr₃) 3430, 1733 cm⁻¹.

Intermediates 24–27 were prepared by a similar procedure to that of Example 2a (Method 1).

Intermediate 24

[1α(Z),2β,3α,5α]-(±)-4-(Acetylamino)phenyl 7-[3-Hydroxy-5-[[3'-methoxy (1,1'-biphenyl)-4-yl]methoxy]-2-(4-morpholinyl)cyclopentyl]-4-heptenoate From Intermediate 13 and 4-(acetylamino)phenol in pyridine. Purification by chromatography initially using (E) then (F) gave the title compound as a foam. I.R. (CHBr₃) 3580, 3430, 1755, 1690, 1510 cm⁻¹.

Intermediate 25

[1α(Z),2β,3α,5α]-(±)-4-Methylphenyl 7-[3-Hydroxy-2-(4-morpholinyl)-5-[(2-phenylthien-4-yl)methoxy]cyclopentyl]-4-heptenoate From Intermediate 14 (0.26 g) and p-cresol (0.286 g). Purification by chromatography (D) gave the title compound as an oil (0.127 g). I.R. (Neat 3450, 1755 cm⁻¹.

Intermediate 26

[1α(Z),2β,3α,5α]-(±)-4-(Methylsulphonyl)phenyl 7-[3-Hydroxy-5-[[4'-methyl(1,1'-biphenyl)-4-yl]methoxy]-2-(4-thiomorpholinyl)cyclopentyl]-4-heptenoate, S-dioxide From Intermediate 15 (0.284 g) and 4-(methylsulphonyl)phenol (0.473 g) using CH₃CN as solvent. Purification by chromatography (G) gave the title compound as a foam (0.312 g). I.R. (CHBr₃) 3580, 3550, 1760 cm⁻¹.

Intermediate 27

[1α(Z),2β,3α,5α]-(±)-L-(−)-[1-(Ethoxycarbonyl)ethyl] 7-[5-[[(1,1'-Biphenyl)-4-yl]methoxy]-3-hydroxy-2-(1-piperidinyl)cyclopentyl]-4-heptenoate Prepared from Intermediate 9 (0.6 g) and L-ethyl lactate (0.385 g) using CH₃CN as solvent. Chromatography (B) gave a mixture (1:1) of the title compound and [1α(Z),2β,3α,5α]-(±)-2-methylpropyl 7-[5-[[(1,1'-biphenyl)-4-yl]methoxy]-3-hydroxy-2-(1-piperidinyl)cyclopentyl]-4-heptenoate as an oil (0.22 g). I.R. (CHBr₃) 3600, 1730 cm⁻¹.

Intermediate 28

[1α(Z),2β,3α,5α]-(±)-(Acetylthio)methyl 7-[5-[[(1,1'-Biphenyl)-4-yl]methoxy]-3-hydroxy-2-(1-piperidinyl)cyclopentyl]-4-heptenoate From Intermediate 9 according to the procedure described for Example 8. Purification by chromatography (F). I.R. (Neat) 3360, 1740, 1705 cm⁻¹.

Intermediate 29

[1α(Z),2β,3α,5α]-(±)-[2-(4-Bromophenyl)-2-oxoethyl] 7-[3-Hydroxy-2-(4-morpholinyl)-5-(2-naphthalenylmethoxy)cyclopentyl]-4-heptenoate From Intermediate 17 and 4-bromophenacyl bromide in an analogous manner to the preparation of Example 6a. Purification by chromatography initially using (G) followed by (B). I.R. (Neat) 3450, 1740, 1700 cm⁻¹.

The preparation of Intermediate 30 is described in British Patent Specification No. 2,028,805A.

Intermediate 30

[1α(Z),2β,5α]-(±)-7-[5-[[(1,1'-Biphenyl)-4-yl]methoxy]-2-(4-morpholinyl)-3-oxocyclopentyl]-5-heptenoic acid.

Intermediate 31

[1α(Z),2β,3β,5α]-(±)-(Acetyloxy)methyl 7-[5-[[(1,1'-Biphenyl)-4-yl]methoxy]-3-hydroxy-2-(4-morpholinyl)cyclopentyl]-4-heptenoate, compound with ethyl acetate (3:1)

To a solution of Intermediate 19 (0.431 g) in pure acetone (4 ml) at 20° was added triethylamine (0.31 ml) followed by bromomethyl acetate (0.305 g) in acetone (2 ml). The mixture was stirred at 20° for 2 h and then poured into pH 6 phosphate buffer (75 ml) and extracted with EA (2×40 ml). The combined extracts were dried, filtered and concentrated, and the residue purified by chromatography (B) to give the title compound as an oil (0.353 g). TLC (F) R_f 0.3. IR (Neat) 3440(br), 1760, 1120 cm⁻¹.

The preparation of Intermediates 32–33 is described in British Patent Specification No. 2,028,805A.

Intermediate 32

[1α(Z),2β,3α,5α]-(±)-Methyl 7-[5-Hydroxy-2-(4-morpholinyl)-3-[(tetrahydro-2H-pyran-2-yl)oxy]cyclopentyl]-5-heptenoate.

Intermediate 33

[1α(Z),2β,3α,5α]-(±)-7-[5-[[(1-1'-Biphenyl)-4-yl]methoxy]-3-hydroxy-2-(4-morpholinyl)cyclopentyl]-5-heptenoic acid.

Intermediate 34

[1α(Z),2β,3β,5α]-(±)-4-(Acetylamino)phenyl 7-[5-[[(1,1'-Biphenyl)-4-yl]methoxy]-3-hydroxy-2-(4-morpholinyl)cyclopentyl]-4-heptenoate, compound with ethyl acetate (5:1)

To a solution of Intermediate 19 (0.5 g) in pure acetone (10 ml) was added triethylamine (0.58 ml) and the mixture cooled to −10° (ice/EtOH). Isobutylchloroformate (0.41 ml) was added, followed after 0.5 h at −10° by 4-(acetylamino)phenol (0.474 g) in acetone (8 ml). After another 0.5 h at −10°, pyridine (1 ml) was added and the temperature allowed to rise to 20° over 2 h. The mixture was poured into 15% pH 6 phosphate buffer solution (100 ml) and extracted with EA (3×50 ml). The combined extracts were dried and evaporated, and the residue purified by chromatography (B) to give the title compound as a viscous gum (0.367 g). TLC (FF) R_f 0.43 IR (CHBr₃) 3420, 3380, 1750, 1685, 1505 cm⁻¹.

Intermediate 35

4-(Bromomethyl)phenyl-4-methoxyphenyl methanone

Benzoyl peroxide (1 g) was added to a solution of 4-methoxyphenyl-4-methylphenyl methanone (22.6 g) and N-bromosuccinimide (17.8 g) in CCl₄ (100 ml). The mixture was heated under reflux for 3.25 h, then cooled to 0°. The precipitated succinimide was filtered off, the filtrate evaporated and the residue purified by crystallisation from cyclohexane to give the title compound (8.9 g), m.p. 76°–78°.

Intermediate 36

[1α(Z),2β,3α,5α]-(±)-7-[5-[4-(4-Methoxybenzoyl)-phenylmethoxy]-2-(4-morpholinyl)-3-[(tetrahydro-2H-pyran-2-yl)oxy]cyclopentyl]-5-heptenoic acid NaH (74% dispersion in oil, 0.74 g) was added in portions over 4.5 h to a solution of Intermediates 32 (0.93 g) and 35 (2.77 g) in DMF (10 ml). After a further 1 h, the mixture was diluted with water (100 ml). Saturated NH$_4$Cl solution (100 ml) was added, the mixture extracted with CH$_2$Cl$_2$ (4×50 ml), the combined extracts were dried and evaporated and the residue purified by chromatography using gradient elution (I) up to (HH) to give the title compound as an oil (1.1 g). I.R. (CHBr$_3$) 3500, 1730–1700(br), 1666 cm$^{-1}$.

Intermediate 37

[1α(Z),2β,3α,5α]-(±)-7-[3-Hydroxy-5-[4-(4-methoxybenzoyl)-phenylmethoxy]-2-(4-morpholinyl)cyclopentyl]-5-heptenoic acid A solution of Intermediate 36 (0.89 g) in acetone (40 ml) and saturated ethereal hydrogen chloride (15 ml) was kept at ambient temperature for 4.5 h. The solvents were removed in vacuo and the residue in pH 6.5 phosphate buffer (50 ml) was extracted with CH$_2$Cl$_2$ (3×40 ml). The combined extracts were dried and evaporated and the residue purified by chromatography (HH) to give the title compound (0.33 g). I.R. (CHBr$_3$) 1730–1700 (br.), 1665 cm$^{-1}$.

Intermediate 38

[1α(Z),2β,3α,5α]-(±)-2-Oxo-2-phenylethyl 7-[5-[[(1,1'-Biphenyl)-4-yl]methoxy]-3-hydroxy-2-(4-morpholinyl)-cyclopentyl]-5-heptenoate A suspension of Intermediate 33 (1 g) in water (10 ml) was treated with potassium t-butoxide (0.234 g) and the resulting solution was added to a solution of phenacyl bromide (0.6 g) in ethanol (10 ml). The mixture was heated under reflux for 4 h, poured into water and extracted with ER. The combined extracts were dried and evaporated and the residue purified by chromatography (G) to give the title compound as an oil (0.9 g). I.R. (CHBr$_3$) 3540 (br.), 1740, 1705 cm$^{-1}$.

Intermediate 39

[1α(Z),2β,3α,5α]-(±)-4-Acetylaminophenyl 7-[5-[[(1,1'-Biphenyl)-4-yl]methoxy]-3-hydroxy-2-(4-morpholinyl)-cyclopentyl]-5-heptenoate Isobutylchloroformate (0.82 ml) was added to a stirred solution of Intermediate 33 (1 g) and triethylamine (1.16 ml) in acetone (10 ml) at −10°. After 0.6 h, N-(4-hydroxyphenyl)acetamide (1.26 g) in acetone (24 ml) containing pyridine (7 drops) was added and stirring continued for a further 0.6 h. The solvent was removed in vacuo and saturated NH$_4$Cl solution (80 ml) added. The mixture was extracted with EA (2×60 ml), the dried extracts evaporated and the residue purified by chromatography (B) to give the title compound as an oil (1.13 g). I.R. (CHBr$_3$) 3425, 1748, 1685 cm$^{-1}$.

The preparation of Intermediates 40–42 is described in British Patent Specification No. 2,070,591A.

Intermediate 40

[1α(Z),2β,3α,5α]-(±)-7-[3-Hydroxy-2-(4-morpholinyl)-5-[4-(phenylmethyl)phenylmethoxy]cyclopentyl]-5-heptenoic acid, hydrochloride.

Intermediate 41

[1α(Z),2β,3α,5α]-(±)-7-[3-Hydroxy-2-(4-morpholinyl)-5-[[(1,1':4',1''-terphenyl)-4-yl]methoxy]cyclopentyl]-5-heptenoic acid, hydrochloride.

Intermediate 42

[1α(Z),2β,3α,5α]-(±)-7-[3-Hydroxy-5-[[(4'-methoxy(1,1'-biphenyl)-4-yl]methoxy]-2-(4-morpholinyl)cyclopentyl]-5-heptenoic acid, hydrochloride.

Intermediate 43

[1α(Z),2β,3α,5α]-(±)-[4-(Aminocarbonyl)phenyl] 7-[3-Hydroxy-5-[[(4'-methoxy(1,1'-biphenyl)-4-yl]methoxy]-2-(4-morpholinyl)cyclopentyl]-5-heptenoate A solution of the base derived from Intermediate 42 (0.5 g) and triethylamine (0.28 ml) in dry CH$_3$CN (30 ml) at −10° was treated with iso-butylchloroformate (0.26 ml) and 0.5 h later with 4-hydroxybenzamide (0.685 g) and dry pyridine (10 ml). After 1.5 h the mixture was poured into pH 6.5 phosphate buffer (100 ml), extracted with EA (2×100 ml), the combined extracts were washed with water (50 ml), dried and evaporated, and the residue purified by chromatography (HH) to give the title compound as a foam (0.49 g). I.R. (CHBr$_3$) 3520, 3400, 1755, 1675 cm$^{-1}$.

Intermediate 44

[1α(Z),2β,3α,5α]-(±)-(Acetylthiomethyl) 7-5[[(1,1'-Biphenyl)-4-yl]methoxy]-3-hydroxy-2-(4-morpholinyl)-cyclopentyl]-5-heptenoate A mixture of Intermediate 33 (0.4 g), bromomethyl thioacetate (0.42 g) and anhydrous K$_2$CO$_3$ (0.23 g) in dry DMF (9 ml) was stirred at 20° for 5.5 h. The mixture was poured into pH 6.5 phosphate buffer (175 ml), extracted with EA (3×60 ml), the combined extracts dried and evaporated, and the residue purified by chromatography (G) to give the title compound as an oil (0.34 g). I.R. (CHBr$_3$) 3520, 1732, 1695 cm$^{-1}$.

EXAMPLE 1

(a) [1α(Z),2β,5α]-(±)-(Methylthio)methyl 7-[5-[[(1',1-Biphenyl)-4-yl]methoxy]-2-(4-morpholinyl)-3-oxocyclopentyl]-4-heptenoate Chloromethyl methyl sulphide (0.11 ml) was added to a stirred solution of Intermediate 1 (0.4 g) and dicyclohexylamine (0.18 ml) in dry CH$_3$CN (6 ml). After 24 h the suspension was poured into saturated NH$_4$Cl solution (40 ml) and extracted with EA (3×30 ml). The combined extracts were dried, filtered, and evaporated to afford a mobile oil. Purification by chromatography (H) gave the title compound as a solid (0.178 g), m.p. 36°–38°. I.R. (Neat) 1740 cm$^{-1}$.

The following compound was prepared by a similar procedure:

(b) [1α(Z),2β,5α]-(±)-(Methylthio)methyl 7-[5-[[4'-Methoxy(1,1'-biphenyl)-4-yl]methoxy]-3-oxo-2-(4-thiomorpholinyl)cyclopentyl)-4-heptenoate, S-dioxide, m.p. 100°–101.5° from Intermediate 2.

Purification initially by chromatography (C) and then by trituration with ER. I.R. (CHBr$_3$) 1740 cm$^{-1}$.

EXAMPLE 2

(a) [1α(Z),2β,5α]-(±)-4-(Acetylamino)phenyl 7-[5-[[(1,1'-Biphenyl)-4-yl]methoxy]-2-(4-morpholinyl)-3-oxocyclopentyl]-4-heptenoate

Method 1

Iso-butylchloroformate (0.20 ml) was added to a cold (−10°) solution of Intermediate 1 (0.24 g) and triethylamine (0.28 ml) in high purity acetone (5 ml). The mixture was stirred for 10 min whereupon 4-(acetylamino)phenol (0.38 g) was added and stirring maintained for a further 2.5 h. Excess solvent was removed in vacuo, the residue treated with pH 6.5 buffer solution (30 ml) and extracted with EA (3×25 ml). The combined extracts were dried, filtered and evaporated to afford a crude product which was dissolved in ER (50 ml) and washed with 8% NaHCO$_3$ solution (2×20 ml) to removed excess phenol. The organic layer was dried, filtered and evaporated, and the residue purified by chromatography (I) to give the title compound as a foam (0.235 g). I.R. (CHBr$_3$) 3420, 1755(sh), 1740, 1685, 1510 cm$^{-1}$. T.L.C. (I) Rf 0.24.

Method 2

To a solution of the compound of Intermediate 34 (0.045 g) in CH$_2$Cl$_2$ (1 ml) at 20° was added triethylamine (0.08 ml) and pyridine sulphur trioxide complex (0.1 g) in DMSO (1 ml). After 2 h the solution was poured into pH 6 phosphate buffer solution (25 ml), extracted with ER (2×25 ml), the combined extracts washed with H$_2$O (20 ml), dried and evaporated. The residue was purified by chromatography (F) to give the title compound (0.028 g). I.R. (CHBr$_3$) 3420, 1755(sh), 1740, 1690, 1510 cm$^{-1}$.

The following compounds were prepared according to the procedure described for Method 1:

(b) [1α(Z),2β,5α]-(±)-2-Methoxyethyl 7-[5[[(1,1′-Biphenyl)-4-yl]methoxy]-2-(4-morpholinyl)-3-oxocyclopentyl]-4-heptenoate, from Intermediate 1 (0.5 g) and 2-methoxyethanol (0.43 ml). Purification by chromatography (N) gave an oil (0.39 g). I.R. (Neat) 1740 cm$^{-1}$.

Analysis Found: C,71.8; H,7.9; N,2.9; C$_{32}$H$_{41}$NO$_6$ requires: C,71,7; H,7.7; N,2.6%

(c) [1α(Z),2β,5α]-(±)-2-(4-Morpholinyl)ethyl 7-[2-(4-Morpholinyl)-3-oxo-5-[4-(phenylmethyl)phenylmethoxy]cyclopentyl]-4-heptenoate, from the free acid derived from Intermediate 3 (0.152 g) and N-2-hydroxyethyl morpholine (0.44 g) in dry CH$_3$CN (6 ml). Purification by chromatography (G) gave an oil (0.071 g). I.R. (CHBr$_3$) 1735 cm$^{-1}$.

Analysis Found: C,71.3; H,8.0; N,4.5; C$_{36}$H$_{48}$N$_2$O$_6$ requires: C,71.5; H,8.0; N,4.6%

(d) [1α(Z),2β,5α]-(±)-2-(Dimethylamino)ethyl 7-[5-[[(1,1′-Biphenyl)-4-yl]methoxy]-2-(4-morpholinyl)-3-oxocyclopentyl]-4-heptenoate, from Intermediate 1 (0.35 g) and N,N-dimethylethanolamine (0.22 ml). Purification by chromatography (O) gave an oil (0.366 g). I.R. (Neat) 1740 cm$^{-1}$ Analysis Found: C,72.2; H,7.7; N,5.2; C$_{33}$H$_{44}$N$_2$O$_5$ requires: C,72.2; H,8.1; N,5.1%

(e) [1α(Z),2β, 5α]-(±)-2-(Acetylamino)phenyl 7-[5-[[(1,1′-Biphenyl)-4-yl]methoxy]-2-(4-morpholinyl)-3-oxocyclopentyl]-4-heptenoate, m.p. 82°-84° from Intermediate 1 (0.477 g) in dry CH$_3$CN (30 ml) and 2-(acetylamino)phenol (0.755 g) in dry pyridine (10 ml). Purification initially by chromatography (P) and then recrystallisation from EA/PE (b.p. 60°-80°) gave 0.102 g of the title compound. I.R. (CHBr$_3$) 3440, 1760, 1740, 1695 cm$^{-1}$.

(f) [1α(Z),2β,5α]-(±)-3-(Acetylamino)phenyl 7-[5-[[(1,1′-Biphenyl)-4-yl]methoxy]-2-(4-morpholinyl)-3-oxocyclopentyl]-4-heptenoate, from Intermediate 1 (0.477 g) in dry CH$_3$CN (30 ml) and 3-(acetylamino)phenol (0.755 g) in dry pyridine (10 ml). Purification by chromatography (P) gave an oil (0.533 g). I.R. (CHBr$_3$) 3470, 1738, 1689, 1520 cm$^{-1}$ Analysis Found: C, 72.3; H, 6.6; N, 4.4; C$_{37}$H$_{42}$N$_2$O$_6$ requires: C 72.8; H, 6.9; N, 4.6%

(g) [1α(Z),2β,5α]-(±)-S-4-(Acetylamino)phenyl 7-[5-[[(1,1′-Biphenyl)-4-yl]methoxy]-2-(4-morpholinyl)-3-oxocyclopentyl]-4-heptenethioate, from Intermediate 1 (0.275 g) and 4-(acetylamino)thiophenol (0.484 g). Purification twice by chromatography, firstly with (Q) and then (E) afforded a foam (0.227 g). I.R. (CHBr$_3$) 3420, 1732, 1690 cm$^{-1}$. T.L.C. (Q) RF 0.22.

(h) [1α(Z),2β,5α(E)]-(±)-1,3-Bis(dimethylamino)-2-propyl 7-[2-(4-Morpholinyl)-3-oxo-5-[(3-phenyl-2-propenyl)-oxy]cyclopentyl]-4-heptenoate, from Intermediate 4 (0.4 g) and 1,3-Bis(dimethylamino)-2-propanol (0.45 ml). Purification by chromatography (R) gave an oil (0.13 g). I.R. (Neat) 1740, 968 cm$^{-1}$ Analysis Found: C, 69.1; H, 9.2; N, 7.5; C$_{32}$H$_{49}$N$_3$O$_5$ requires: C, 69.2; H, 8.9; N, 7.6%

(i) [1α(Z),2β,5α]-(±)-2,2,2-Trichloroethyl 7-[5-[[(1,1′-Biphenyl)-4-yl]methoxy]-2-(4-morpholinyl)-3-oxocyclopentyl]-4-heptenoate, m.p. 86.5°-88° (from Intermediate 1 (0.8 g) and 2,2,2-trichloroethanol (0.76 ml). Purification initially by chromatography (S) and then by trituration with ER gave a solid (0.22 g). I.R. (CHBr$_3$) 1740 cm$^{-1}$.

Analysis Found: C, 61.3; H, 5.9; N, 2.4; C$_{31}$H$_{36}$Cl$_3$NO$_5$ requires: C, 61.0; H, 6.0; N, 2.3%

(j) [1α(Z),2β,5α]-(±)-3,3,5-Trimethylcyclohexyl 7-[5-[[(1,1′-Biphenyl)-4-yl]methoxy]-2-(4-morpholinyl)-3-oxocyclopentyl]-4-heptenoate, from Intermediate 1 (1.09 g) in acetone (12 ml) and 3,3,5-trimethylcyclohexanol (1.028 g) in dry pyridine (8 ml). Purification by chromatography (X) gave an oil (0.114 g). I.R. (Neat) 1740 cm$^{-1}$. T.L.C. (X) Rf 0.1.

(k) [1α(Z),2β,5α]-(±)-S-2-(methoxythio)ethyl 7-[5-[[(1,1′-Biphenyl)-4-yl]methoxy]-2-(4-morpholinyl)-3-oxocyclopentyl]-4-heptenethioate, m.p. 35°-37° from Intermediate 1 (0.66 g) in dry CH$_3$CN (40 ml) and 2-(methylthio)ethane thiol (0.68 g) in dry pyridine (10 ml). Purification initially by chromatography (C) and then by trituration with ice-cold PE (b.p. 40°-60°) gave a solid (0.251 g). I.R. (CHBr$_3$) 1740, 1690 cm$^{-1}$.

(l) [1α(Z),2β,5α]-(±)-2-Propenyl 7-[5-[[(1,1′-Biphenyl)-4-yl]methoxy]-2-(4-morpholinyl)-3-oxocyclopentyl]-4-heptenoate, from Intermediate 1 (0.57 g) and 2-propen-1-ol (1.8 ml.). Purification by chromatography (K) gave an oil (0.17 g). I.R. (Neat) 1735 cm$^{-1}$.

Analysis Found: C, 74.2; H, 7.5; N, 2.7; C$_{32}$H$_{39}$NO$_5$ requires: C, 74.25; H, 7.6; N, 2.7%.

(m) [1α(Z),2β,5α]-(±)-(2-Furanylmethyl) 7-[5-[[(1,1′-Biphenyl)-4-yl]methoxy]-2-(4-morpholinyl)-3-oxocyclopentyl]-4-heptenoate, compound with water (1:0.5), from Intermediate 1 (0.5 g) and 2-furanmethanol (0.616 g). Purification by chromatography (V) gave an oil (0.442 g). I.R. (Neat) 3665, 1739 cm$^{-1}$ Analysis Found: C, 72.3; H, 7.1; N, 2.4; C$_{34}$H$_{39}$NO$_6$.0.5H$_2$O requires: C, 72.0; H, 7.0; N, 2.5%.

EXAMPLE 3

(a) [1α(Z),2β,5α]-(±)-Acetyloxy)methyl 7-[5-[[(1,1′-Biphenyl)-4-yl]methoxy]-2-(4-morpholinyl)-3-oxocyclopentyl]-4-heptenoate

Method 1

Bromomethyl acetate (0.12 g) was added to a solution of Intermediate 1 (0.25 g) and triethylamine (0.146 ml) in acetone (5 ml) and the mixture stirred at room temperature for 2.5 h. The mixture was poured into water (100 ml) and extracted with ER (4×40 ml). The organic layers were dried and evaporated to give an oil (0.287 g). Purification by chromatography (J) gave the title compound as a solid (0.175 g), m.p. 35°–37°. I.R. (CHBr$_3$) 1760, 1740 cm$^{-1}$.

Method 2

To a cold (0°), stirred solution of Intermediate 21a (0.19 g) in acetone (10 ml) was added Jones reagent (2.67 M, 0.17 ml). The mixture was kept at 0° for 6 h, whereupon IPA (0.5 ml) was added, followed 10 min later by 8% NaHCO$_3$ solution (35 ml). The resulting suspension was extracted with EA (2×40 ml). The dried extracts were evaporated and the residue purified by chromatography (K) to give the title compound (0.056 g). I.R. (CHBr$_3$) 1760, 1740 cm$^{-1}$.

Method 3

To a solution of the compound of Intermediate 31 (0.054 g) in CH$_2$Cl$_2$ (0.75 ml) was added triethylamine (0.15 ml), followed by pyridine sulphur trioxide complex (0.13 g) in DMSO (1 ml). The mixture was stirred at 21° for 1 h, poured into pH 6 phosphate buffer solution (30 ml) and extracted with ER (2×25 ml). The combined extracts were dried and evaporated and the residue purified by chromatography (C) to give the title compound (0.04 g). I.R. (CHBr$_3$) 1760, 1740 cm$^{-1}$.

Method 4

Lindlar catalyst (0.007 g) was hydrogenated at 18° and atmospheric pressure in EA (4 ml) containing quinoline (0.003 g) until uptake ceased. A solution of Intermediate 21b (0.04 g) in EA (4 ml) was added and hydrogenation continued for 54 min (uptake ceased). The catalyst was filtered off, the filtrate evaporated and the residue purified by chromatography (L) to give the title compound (0.039 g). I.R. (CHBr$_3$) 1760, 1740 cm$^{-1}$.

The following compounds were prepared using a similar manner to Method 1.

(b) [1α(Z),2β,5α]-(±)-1-(Acetyloxy)ethyl 7-[5-[[(1,1'-Biphenyl)-4-yl]methoxy]-2-(4-morpholinyl)-3-oxocyclopentyl]-4-heptenoate, compound with diethyl ether (10:1), from Intermediate 1 (0.435 g) and 1-bromoethyl acetate (0.456 g). Purification by chromatography (T) gave an oil (0.234 g). I.R. (Neat) 1760, 1745 cm$^{-1}$ Analysis Found: C, 69.8; H, 7.6; N, 2.4; C$_{33}$H$_{41}$NO$_7$.0.1C$_4$H$_{10}$O requires: C, 70.2; H, 7.4; N, 2.4%.

(c) [1α(Z),2β,5α]-(±)-(Acetyloxy)methyl 7-[5-[[(1,1'-Biphenyl)-4-yl]methoxy]-3-oxo-2-(4-thiomorpholinyl)-cyclopentyl]-4-heptenoate, from Intermediate 5 (0.251 g) and bromomethyl acetate (0.155 g). Purification by chromatography (U) afforded an oil (0.211 g). I.R. (Neat) 1765, 1745 cm$^{-1}$.

Analysis Found: C, 67.9; H, 6.9; N, 2.45; C$_{32}$H$_{39}$NO$_6$S requires: C, 67.9; H, 6.95; N, 2.5%

EXAMPLE 4

[1α(Z),2β,5α]-(±)-Triphenylmethyl 7-[5-[[(1,1'-Biphenyl)-4-yl]methoxy]-2-(4-morpholinyl)-3-oxocyclopentyl]-4-heptenoate From Intermediate 1 (1.5 g) and triphenylmethyl chloride (1.315 g) in CH$_2$Cl$_2$ (9 ml), according to the method described for Example 3a (Method 1). Purification by chromatography (C) gave a foam (1.843 g). I.R. (CHBr$_3$) 1740 cm$^{-1}$.

Analysis Found: C, 80.2; H, 6.9; N, 2.1; C$_{48}$H$_{49}$NO$_5$ requires: C, 80.1; H, 6.9; N, 1.95%.

EXAMPLE 5

[1α(Z),2β,5α]-(±)-(Ethoxycarbonyl)methyl 7-[5-[[(1,1'-Biphenyl)-4-yl]methoxy]-2-(4-morpholinyl)-3-oxocyclopentyl]-4-heptenoate

Method 1

From Intermediate 1 (0.3 g) and ethyl bromoacetate (0.222 ml) in dry CH$_3$CN (5 ml) using the procedure described for Example 3a, Method 1. Purification by chromatography (V) gave an oil (0.329 g). I.R. (Neat) 1750 (sh), 1740 cm$^{-1}$ Analysis Found: C, 70.3; H, 7.7; N, 2.1; C$_{33}$H$_{41}$NO$_7$ requires: C, 70.3; H, 7.3; N, 2.5%.

Method 2

A solution of Intermediate 1 (0.245 g) and ethyl diazoacetate (0.065 ml) in dioxan (5 ml) containing copper (II) chloride (0.003 g) was stirred for 18 h at room temperature. The reaction mixture was poured into pH 6 phosphate buffer (40 ml) and extracted with CH$_2$Cl$_2$ (3×30 ml). The combined extracts were dried and evaporated, and the residue purified by chromatography (H) to give the title compound (0.119 g). I.R. (Neat) 1750 (sh), 1740 cm$^{-1}$.

EXAMPLE 6

(a) [1α(Z),2β,5α]-(±)-2-Oxo-2-phenylethyl 7-[5-[[(1,1'-Biphenyl)-4-yl]methoxy]-2-(4-morpholinyl)-3-oxocyclopentyl]-4-heptenoate α-Bromoacetophenone (0.252 g) was added to a stirred solution of Intermediate 1 (0.3 g) and diisopropylethylamine (0.24 ml) in dry CH$_3$CN (8 ml). After 1 h the solution was poured into pH 6.5 buffer (30 ml) and extracted with EA (3×25 ml). The combined extracts were dried, filtered and evaporated, and the residue purified by chromatography (N) to afford the title compound as an oil (0.353 g). I.R. (Neat) 1740, 1700 cm$^{-1}$.

Analysis Found: C, 74.1; H, 7.3; N, 2.1; C$_{37}$H$_{41}$NO$_6$ requires: C, 74.6; H, 6.9; N, 2.4%.

The following compound was prepared in a similar manner:

(b) [1α(Z),2β,5α]-(±)-Tetrahydro-2-oxofuran-3-yl-7-[5-[[(1,1'-Biphenyl)-4-yl]methoxy]-2-(4-morpholinyl)-3-oxocyclopentyl]-4-heptenoate from Intermediate 1 (0.3 g) and 3-bromo-dihydro-2(3H)-furanone (0.24 ml). Purification by chromatography (C) gave an oil (0.272 g). I.R. (Neat) 1790, 1740 cm$^{-1}$. T.L.C. (C) Rf 0.24.

EXAMPLE 7

[1α(Z),2β,5α]-(±)-Tetrahydro-5-oxofuran-2-yl 7-[5-[[(1,1'-Biphenyl)-4-yl]methoxy]-2-(4-morpholinyl)-3-oxocyclopentyl]-4-heptenoate 5-Chloro-dihydro-2(3H)-furanone (0.152 g) was added to a mixture of Intermediate 1 (0.2 g) and trioctylpropyl ammonium bromide (0.4 g) in diisopropylethylamine (0.44 ml) and dry CH$_3$CN (3 ml). The mixture was stirred at room temperature for 2 h, poured into aqueous pH 6.5 phosphate buffer (65 ml) and then extracted with EA (3×20 ml). The dried extracts were evaporated and the residue purified by chromatography (W) to give the title compound as an oil (0.16 g). I.R. (Neat) 1800, 1750 cm$^{-1}$ T.L.C. (C) Rf 0.23.

EXAMPLE 8

[1α(Z),2β,5α]-(±)-(Acetylthio)methyl 7-[5-[[(1,1'-Biphenyl)-4-yl]methoxy]-2-(4-morpholinyl)-3-oxocyclopentyl]-4-heptenoate Bromomethylthioacetate (0.377 g) was added to a mixture of Intermediate 1 (0.426 g) and anhydrous K$_2$CO$_3$ (0.246 g) in dry DMF (8 ml) and the mixture then stirred for 3 h. The mixture was poured into aqueous pH 6.5 phosphate buffer (170 ml) and extracted with EA (3×60 ml). The combined organic layers were dried and evaporated, and the residue purified by chromatography (C) to give the title compound as an oil (0.269 g). I.R. (Neat) 1740, 1708 cm$^{-1}$. T.L.C. (C) Rf 0.44.

EXAMPLE 9

(a) [1α(Z),2β,5α]-(±)-(Methylthio)methyl 7-[5-[[4'-Methoxy(1,1'-biphenyl)-4-yl]methoxy]-2-(4-morpholinyl)-3-oxocyclopentyl]-4-heptenoate Pyridinium trifluoroacetate (0.375 g) was added to a stirred mixture of Intermediate 6 (0.5 g) and dicyclohexylcarbodiimide (1 g) in dry DMSO (5 ml), under nitrogen, with water bath cooling. After 5.5 h, the mixture was diluted with H$_2$O (130 ml) and extracted with CH$_2$Cl$_2$ (3×50 ml). The organic solution was dried (Na$_2$SO$_4$) and evaporated in vacuo to leave a semi-solid (1.5 g) which was triturated with ER (4×5 ml), the solid filtered off and the ER solution evaporated to give an oil (1 g). Chromatography (H) gave, after trituration with ER, the title compound (0.31 g) as a solid m.p. 68°-72°. I.R. (CHBr$_3$) 1740 cm$^{-1}$.

The following compounds were similarly prepared:

(b) [1α(Z),2β,5α]-(±)-(Methylthio)methyl 7-[5-[[4'-Methyl(1,1'-biphenyl)-4-yl]methoxy]-2-(4-morpholinyl)-3-oxocyclopentyl]-4-heptenoate, m.p. 56.5°-59.5° from Intermediate 7 (0.3 g). Purification by chromatography (N) gave an oil (0.14 g) which crystallised on standing. I.R. (CHBr$_3$) 1735 cm$^{-1}$.

(c) [1α(Z),2β,5α(E)]-(±)-(Methylthio)methyl 7-[2-(4-Morpholinyl)-3-oxo-5-[(3-Phenyl-2-propenyl)oxy]-cyclopentyl]-4-heptenoate, from Intermediate 8 (0.257 g). Purification by chromatography (T) gave an oil (0.136 g). I.R. (Neat) 1735, 970 cm$^{-1}$ Analysis Found: C, 66.3; H,7.6; N, 2.9; C$_{27}$H$_{37}$NO$_5$S requires: C,66.5; H,7.7; N,2.9%.

EXAMPLE 10

[1α(Z),2β,5α]-(±)-(Methylthio)methyl 7-[5-[[1,1'-Biphenyl)-4-yl]methoxy]-3-oxo-2-(1-piperidinyl)cyclopentyl]-4-heptenoate To a solution of Intermediate 9 (0.37 g) and dicyclohexylcarbodiimide (0.64 g) in DMSO (8 ml) at 20° was added pyridinium trifluoroacetate (0.254 g) and the mixture stirred for 2 h. Aqueous pH 6 phosphate buffer (75 ml) was added and the mixture extracted with ER (2×50 ml). The combined extracts were dried and evaporated and the residue partially purified by chromatography (L) to give an oil (0.224 g). A portion (0.097 g) of this material was converted into its maleate salt by the addition of an excess of an ER solution of maleic acid. The resultant oily precipitate was triturated with ER (5×3 ml) and then converted back to the free base by the addition of pH 6 phosphate buffer (10 ml) and extraction with ER (3×10 ml). Finally, chromatography (C) afforded pure title compound as an oil (0.047 g). I.R. (Neat) 1740 cm$^{-1}$ T.L.C. (L) Rf 0.27.

EXAMPLE 11

[1R-[1α(Z),2β,5α]]-(−)-(Methylthio)methyl 7-[5-[[(1,1'-Biphenyl)-4-yl]methoxy]-2-(4-morpholinyl)-3-oxocyclopentyl]-4-heptenoate A solution of Intermediate 10 (0.43 g) in CH$_3$CN (3 ml) containing triethylamine (0.3 ml) was added to a stirred mixture of chloromethylmethylsulphide (0.15 ml) and NaI (0.05 g) in CH$_3$CN (1 ml) at room temperature. The mixture was stirred at room temperature for 4 h and then kept at 0° overnight. The mixture was diluted with pH 6.5 phosphate buffer (75 ml) and extracted with ER (3×50 ml). The combined extracts were dried and evaporated and the residue was purified by chromatography (M) to give the title compound as an oil (0.136 g) which solidified on standing, m.p. 48°-50°. $[α]_D^{21.5} = -9.0°$ (CHCl$_3$). I.R. (CHBr$_3$) 1735 cm$^{-1}$.

EXAMPLE 12

[1α(Z),2β,5α]-(±)-3-(Acetylamino)propyl 7-[5-[[(1,1'-Biphenyl)-4-yl]methoxy]-2-(4-morpholinyl)-3-oxocyclopentyl]-4-heptenoate A solution of Intermediate 1 (0.477 g) in dry CH$_3$CN (30 ml) containing triethylamine (0.28 ml) was cooled to −10° under dry nitrogen and treated with isobutylchloroformate (0.26 ml). After stirring at −10° for 1 h a solution of N-3-hydroxypropylacetamide (0.585 g) in dry pyridine (10 ml) was added and the mixture allowed to warm to room temperature over 2 h. The mixture was poured into pH 6 phosphate buffer (100 ml), extracted into EA (2×100 ml), the combined extracts were washed with H$_2$O (4×50 ml), aqueous CuSO$_4$ (2×50 ml), H$_2$O (50 ml) and brine (50 ml), dried and evaporated. Purification of the residue by chromatography (G) gave the title compound as an oil (0.103 g). I.R. (Neat) 3310, 1740, 1680, 1550 cm$^{-1}$ Analysis Found: C,70.4; H,8.1; N,4.8; C$_{34}$H$_{44}$N$_2$O$_6$ requires: C,70.8; H,7.7; N,4.9%.

EXAMPLE 13

[1R-[1α(Z),2β,5α]]-(−)-(Acetyloxy)methyl 7-[5-[[1,1'-Biphenyl)-4-yl]methoxy]-2-(4-morpholinyl)-3-oxocyclopentyl]-4-heptenoate A solution of Intermediate 10 (0.436 g) in acetone (6 ml) containing triethylamine (0.3 ml) and bromomethylacetate (0.3 g) was stirred at 20° for 2 h. The mixture was poured into pH 6.5 phosphate buffer (50 ml) and extracted with ER (3×50 ml). The combined extracts were dried and evaporated to give an oil (0.45 g). Purification by chromatography (C) gave the title compound as an oil (0.351 g). $[\alpha]_D^{21.5} = -8.8°$ (CHCl$_3$). I.R. (Neat) 1765, 1740 cm$^{-1}$ Analysis Found: C,69.8; H,7.3; N,2.4; C$_{32}$H$_{39}$NO$_7$ requires: C,69.9; H,7.15; N,2.55%.

EXAMPLE 14

[1α(Z),2β,5α]-(±)-2-Amino-2-oxoethyl 7-[5-[[(1,1'-Biphenyl)-4-yl]methoxy]-2-(4-morpholinyl)-3-oxocyclopentyl]-4-heptenoate A mixture of Intermediate 1 (0.3 g), NaI (0.12 g), chloroacetamide (0.294 g) and dicyclohexylamine (0.12 ml) in dry DMF (3 ml) was stirred under nitrogen for 20 h. The suspension was poured into pH 6.5 buffer solution (30 ml) and extracted with EA (3×25 ml). The combined extracts were washed with brine (30 ml), dried, filtered and evaporated to afford a mobile oil (0.7 g). Chromatography (E) gave impure title compound (0.272 g) as an oil. The oil was dissolved EA (20 ml) washed with H$_2$O (30 ml) and brine (30 ml), dried, filtered and evaporated to give a viscous oil (0.2 g). On taking up into EA/PE (b.p. 60°–80°) the title compound crystallised out (0.157 g), m.p. 94°–94.5°. I.R. (CHBr$_3$) 3520, 3400, 1735, 1690, 1665 cm$^{-1}$.

EXAMPLE 15

[1α(Z),2β,5α]-(±)-S-(2-Pyridinyl) 7-[5-[[(1,1'-Biphenyl)-4-yl]methoxy]-2-(4-morpholinyl)-3-oxocyclopentyl]-4-heptenethioate 2,2-Dipyridyldisulphide (0.070 g) was added to a stirred solution of Intermediate 1 (0.1 g) and triphenylphosphine (0.084 g) in benzene (0.6 ml). After 3 days the mixture was poured into pH 6.5 buffer solution (30 ml) and extracted into EA (3×25 ml). The combined extracts were dried, filtered and evaporated, and the residue purified by chromatography (C) to give the title compound as an oil (0.1 g). I.R. (Neat) 1738, 1705 cm$^{-1}$ T.L.C. (C) Rf 0.24.

EXAMPLE 16

(a) [1α(Z),2β,5α]-(±)-Methoxymethyl 7-[5-[3-[(1,1'-Biphenyl)-4-yl]-propoxy]-2-(4-morpholinyl)-3-oxocyclopentyl]-4-heptenoate Pyridine sulphur trioxide complex (0.193 g) in dry DMSO (2 ml) was added to a cold (0°) mixture of Intermediate 22 (0.22 g), triethylamine (0.45 ml), dry DMSO (2 ml) and dry CH$_2$Cl$_2$ (2 ml). After stirring for 1.5 h H$_2$O (4 ml) was added and excess CH$_2$Cl$_2$ removed in vacuo. The residue was treated with citric acid (0.22 g) in H$_2$O (4 ml) and extracted with EA (3×20 ml). The combined extracts were dried, filtered and evaporated and the residue purified by chromatography (N) to give pure title compound as an oil (0.175 g). I.R. (CHBr$_3$) 1735 cm$^{-1}$ Analysis Found: C,71.8; H,8.0; N,2.5; C$_{33}$H$_{43}$NO$_6$ requires: C,72.1; H,7.9; N,2.6%.

The following compounds were similarly prepared:

(b) [1α(Z),2β,5α]-(±)-(Methylthio)methyl 9-[5-[[(1,1'-Biphenyl)-4-yl]methoxy]-2-(4-morpholinyl)-3-oxocyclopentyl]-6-nonenoate, from Intermediate 23 (0.25 g). Purification by chromatography (Y) gave an oil (0.166 g). I.R. (Neat) 1740 cm$^{-1}$ Analysis Found: C,70.0; H,7.9; N,2.4; C$_{33}$H$_{43}$NO$_5$S requires: C,70.0; H,7.7; N,2.5%.

(c) [1α(Z),2β,5α]-(±)-4-(Acetylamino)phenyl 7-[5-[[3'-Methoxy(1,1'-biphenyl)-4-yl]methoxy]-2-(4-morpholinyl)-3-oxocyclopentyl]-4-heptenoate, from Intermediate 24 (0.206 g). Purification by chromatography initially (C) followed by (E) gave a foam (0.182 g). I.R. (CHBr$_3$) 3420, 1755, 1740, 1690, 1520 cm$^{-1}$ T.L.C. (E) Rf 0.26

(d) [1α(Z),2β,5α]-(±)-(4-Methylphenyl 7-[2-(4-Morpholinyl)-3-oxo-5-[(2-phenylthien-4-yl)methoxy]cyclopentyl]-4-heptenoate, m.p. 78°–80° from Intermediate 25 (0.21 g). Purification by chromatography (Z) gave an oil (0.104 g) which solidified on standing. I.R. (Nujol) 1760, 1742 cm$^{-1}$ Analysis Found: C,70.7; H,6.9; N,2.1; C$_{34}$H$_{39}$NO$_5$S requires: C,71.2; H,6.85; N,2.4%.

(e) [1α(Z),2β,5α]-(±)-4-(Methylsulphonyl)phenyl 7-[5-[[4'-Methyl (1,1'-biphenyl)-4-yl]methoxy]-3-oxo-2-(4-thiomorpholinyl)cyclopentyl]-4-heptenoate, S-dioxide, from Intermediate 26 (0.312 g). Purification by chromatography (I) gave a foam (0.191 g). I.R. (CHBr$_3$) 1760, 1745 cm$^{-1}$ Analysis Found: C,63.6; H,6.2; N,1.8; C$_{27}$H$_{43}$NO$_8$S$_2$ requires: C,64.0; H,6.2; N,2.0%.

(f) [1α(Z),2β,5α]-(±)-L-(−)-1-(Ethoxycarbonyl)ethyl 7-[5-[[(1,1'-Biphenyl)-4-yl]methoxy]-3-oxo-2-(1-piperidinyl)cyclopentyl]-4-heptenoate, from the product mixture of Intermediate 27 (0.2 g). Purification by chromatography (AA) gave an oil (0.046 g). I.R. (CHBr$_3$) 1740 (sh), 1732 cm$^{-1}$ Analysis Found: C,73.0; H,8.1; N,2.7; C$_{35}$H$_{45}$NO$_6$ requires: C,73.0; H,7.9; N,2.4%.

(g) [1α(Z),2β,5α]-(±)-(Acetylthio)methyl 7-[5-[[(1,1'-Biphenyl)-4-yl]methoxy]-3-oxo-2-(2-(1-piperidinyl)cyclopentyl]-4-heptenoate, from Intermediate 28 (0.089 g). Chromatography initially (L) followed by (V) gave an oil (0.05 g). I.R. (CHBr$_3$) 1733, 1700 cm$^{-1}$ T.L.C. (C) Rf 0.59

(h) [1α(Z),2β,5α]-(±)-(Acetyloxy)methyl 7-[2-(4-Morpholinyl)-3-oxo-5-[4-(thien-2-yl)phenylmethoxy]-cyclopentyl]-4-heptenoate, m.p. 78°–80.5° from Intermediate 21c. Purification initially by chromatography (BB) and then by recrystallisation from ER/isopentane. I.R. (CHBr$_3$) 1740 cm$^{-1}$ (i) [1α(Z),2β,5α]-(±)-2-(4-Bromophenyl)-2-oxoethyl 7-[2-(4-Morpholinyl)-5-(2-naphthalenylmethoxy)-3-oxocyclopentyl]-4-heptenoate, from Intermediate 29 (0.889 g). Purification by chromatography (CC) gave an oil (0.704 g). I.R. (Neat) 1745, 1708 cm$^{-1}$ Analysis Found: C,64.8; H,6.0; N,1.9; C$_{35}$H$_{38}$BrNO$_6$ requires: C,64.8; H,5.9; N,2.2%.

EXAMPLE 17

[1α(Z),2β,5α]-(±)-(Benzoyloxy)methyl 7-[5-[[(1,1'-Biphenyl)-4-yl]methoxy]-2-(4-morpholinyl)-3-oxocyclopentyl]-4-heptenoate To a solution of Intermediate 1 (0.477 g), sodium iodide (0.3 g) and triethylamine (0.3 ml) in acetone (5 ml) was added chloromethylbenzoate (0.34 g). After 4 h further quantities of chloromethylbenzoate (0.68 g) and triethylamine (0.6 ml) were added and stirring maintained for 20 h. The reaction mixture was poured into pH 6.5 phosphate buffer (50 ml) and partitioned with CH$_2$Cl$_2$ (3×50 ml). The dried extracts were evaporated to give a semi-solid (0.95 g). Purification by chromatography (EE) gave the title compound as an oil (0.31 g). I.R. (Neat) 1740 cm$^{-1}$ Analysis Found: C,73.1; H,7.15; N,2.1; C$_{37}$H$_{41}$NO$_7$ requires: C,72.65; H,6.8; N,2.3%.

EXAMPLE 18

[1α(Z),2β,5α]-(±)-S-Methoxymethyl 7-[4-[[(1,1'-Biphenyl)-4-yl]methoxy]-2-(4-morpholinyl)-3-oxocyclopentyl]-4-heptenethioate Isobutylchloroformate (0.19 ml) was added to a solution of Intermediate 1 (0.527 g) and triethylamine (0.4 ml) in dry DMF (4 ml), under nitrogen, at 0°. After 0.5 h sodium hydrogen sulphide (0.185 g) was added and the mixture stirred at room temperature for 1 h. The suspension was cooled (0°) and triethylamine (0.46 ml) added followed by chloromethyl methyl ether (0.25 ml). After a further 1 h the mixture was poured into pH 6.5 phosphate buffer (150 ml) and extracted with EA (3×50 ml). The dried organic extracts were evaporated in vacuo to give an oil (0.72 g). Purification by chromatography (DD) gave the title compound as an oil (0.4 g). I.R. (Neat) 1740, 1695 cm$^{-1}$ Analysis Found: C,68.9; H,7.4; N,2.6; $C_{31}H_{39}NO_5S$ requires: C,69.2; H,7.4; N,2.6%.

EXAMPLE 19

(a) [1α(Z),2β,5α]-(±)-(Methylthio)methyl 7-[5-[[1,1'-Biphenyl)-4-yl]methoxy]-2-(4-morpholinyl)-3-oxocyclopentyl]-5-heptenoate Pyridinium trifluoroacetate (0.3 g) was added to a stirred solution of Intermediate 33 (0.48 g) and dicyclohexylcarbodiimide (0.82 g) in dry DMSO (4 ml) at ambient temperature. After 5 h, the mixture was poured into water (25 ml) and extracted with $CH_2Cl_2$ (3×25 ml). The combined extracts were dried and evaporated and the residue was purified by chromatography (H) to give the title compound (0.25 g) as a solid, m.p. 45°-47°.

Analysis Found: C, 69.7; H, 7.6; N, 2.7; $C_{31}H_{39}NO_5S$ requires: C, 69.3; H, 7.3; N, 2.6%. The following compounds were prepared by a similar procedure:

(b) [1α(Z),2β,5α]-(±)-(Methylthio)methyl 7-[5-[4-(4-Methoxybenzoyl)phenylmethoxy]-2-(4-morpholinyl)-3-oxocyclopentyl]-5-heptenoate, from Intermediate 37 Purification by chromatography (I). T.L.C. (I) $R_f$ 0.39

Analysis Found: C, 66.2; H, 6.95; N, 2.4; $C_{33}H_{41}NO_7S$ requires: C, 66.5; H, 6.90; N, 2.35%.

(c) [1α(Z),2β,5α]-(±)-(Methylthio)methyl 7-[2-(4-Morpholinyl)-3-oxo-5-[4-(phenylmethyl)phenylmethoxy]cyclopentyl]-5-heptenoate, from Intermediate 40 Purification by chromatography (C) I.R. (CHBr$_3$) 1738 cm$^{-1}$ Analysis Found: C, 69.6; H, 7.25; N, 2.6; $C_{33}H_{41}NO_5S$ requires: C, 69.7; H, 7.5; N, 2.5%.

(d) [1α(Z),2β,5α]-(±)-(Methylthio)methyl 7-[2-(4-Morpholinyl)-3-oxo-5-[[1,1':4',1''-terphenyl]-4-yl]methoxy]cyclopentyl]-5-heptenoate, m.p. 115°-118° from Intermediate 41. Purification initially by chromatography (C) and then by crystallisation (EA-PE).

Analysis Found: C, 72.6; H, 7.0; N, 2.4; $C_{37}H_{43}NO_5S$ requires: C, 72.4; H, 7.1; N, 2.3%.

EXAMPLE 20

(a) [1α(Z),2β,5α]-(±)-2-(Dimethylamino)ethyl 7-[5-[[(1,1'-Biphenyl)-4-yl]methoxy]-2-(4-morpholinyl)-3-oxocyclopentyl]-5-heptenoate A solution of Intermediate 30 (0.5 g) and triethylamine (0.29 ml) in acetone (10 ml) at −10° was treated with isobutyl chloroformate (0.28 ml) and 15 min later with N,N-dimethyl ethanolamine (0.22 ml). The cooling bath was removed and stirred continued at ambient temperature for 5 h. The mixture was poured into 8% NaHCO$_3$ solution (20 ml) and extracted with EA (3×30 ml). The combined extracts were washed with brine (50 ml), dried and evaporated. The residue was purified initially by chromatography (O) and then by recrystallisation [ether-PE (b.p. 60°-80°)] to give the title compound (0.25 g), m.p. 72°-73°.

Analysis Found: C, 71.8; H, 7.8; N, 4.8; $C_{33}H_{44}N_2O_5$ requires: C, 72.2; H, 8.1; N, 5.1%. The following compounds were prepared by a similar procedure:

(b) [1α(Z),2β,5α]-(±)-Phenyl 7-[5-[[(1,1'-Biphenyl)-4-yl]methoxy]-2-(4-morpholinyl)-3-oxocyclopentyl]-5-heptenoate, m.p. 72.5°-74°, from Intermediate 30 and phenol. Purification by chromatography (M).

Analysis Found: C, 75.9; H, 7.1; N, 2.7; $C_{35}H_{39}NO_5$ requires: C, 75.9; H, 7.1; N, 2.5%.

(c) [1α(Z),2β,5α]-(±)-4-Methoxyphenyl 7-[5-[[(1,1'-Biphenyl)-4-yl]methoxy]-2-(4-morpholinyl)-3-oxocyclopentyl]-5-heptenoate, m.p. 75°-76.5°, from Intermediate 30 and 4-methoxyphenol. Purification by chromatography (M).

Analysis Found: C, 74.25; H, 7.1; N, 2.4; $C_{36}H_{41}NO_5$ requires: C, 74.1; H, 7.1; N, 2.4%.

(d) [1α(Z),2β,5α]-(±)-4-Acetylphenyl 7-[5-[[1,1'-Biphenyl)-4-yl]methoxy]-2-(4-morpholinyl)-3-oxocyclopentyl]-5-heptenoate, m.p. 73°-75°, from Intermediate 30 and 1-(4-hydroxyphenyl)ethanone. Purification by chromatography (C) and trituration with ER.

Analysis Found: C, 74.75; H, 6.8; N, 2.5; $C_{37}H_{41}NO_6$ requires: C, 74.6; H, 6.9; N, 2.35%.

(e) [1α(Z),2β,5α]-(±)-4-Methylphenyl 7-[5-[[(1,1'-Biphenyl)-4-yl]methoxy]-2-(4-morpholinyl)-3-oxocyclopentyl]-5-heptenoate, m.p. 81°-83°, from Intermediate 30 and 4-methylphenol. Purification by chromatography (M)

Analysis Found: C, 75.9; H, 7.2; N, 2.5; $C_{36}H_{41}NO_5$ requires: C, 76.15; H, 7.3; N, 2.5%.

(f) [1α(Z),2β,5α]-(±)-4-[[7-[5-[[(1,1'-Biphenyl)-4-yl]methoxy]-2-(4-morpholinyl)-3-oxocyclopentyl]-5-heptenoyl]-oxy]benzoic acid, m.p. 95°-102° from Intermediate 30 and 4-hydroxybenzoic acid using pyridine as co-solvent. The reaction mixture was poured into 0.1 M KH$_2$PO$_4$ solution and extracted with ER. The ER extract was washed with 0.2 M sulphuric acid, pH 6.5 phosphate buffer, dried and evaporated. The residue was purified initially by chromatography (C) and then by crystallisation from ether-isopentane.

Analysis Found: C, 71.9; H, 6.9; N, 2.5; $C_{36}H_{39}NO_7$ requires: C, 72.3; H, 6.6; N, 2.3%.

EXAMPLE 21

[1α(Z),2β,5α]-(±)-2-Oxo-2-phenylethyl 7-[5-[[(1,1'-Biphenyl)-4-yl]methoxy]-2-(4-morpholinyl)-3-oxocyclopentyl]-5-heptenoate A well stirred solution of Intermediate 38 (0.7 g) in DMSO (15 ml) and triethylamine (5 ml) was treated with pyridine-sulphur trioxide complex (0.65 g) and was kept at ambient temperature for 0.8 h. The mixture was poured into saturated NH$_4$Cl solution (100 ml) and extracted with CH$_2$Cl$_2$ (3×70 ml). The combined extracts were dried and evaporated and the residue was purified by chromatography (C) to give the title compound as an oil 0.56 g. I.R. (Neat) 1740, 1700 cm$^{-1}$ Analysis Found: C, 74.25; H, 6.8; N, 2.3; $C_{37}H_{41}NO_6$ requires: C, 74.6; H, 6.9; N, 2.35%.

EXAMPLE 22

[1α(Z),2β,5α]-(±)-4-Acetylaminophenyl 7-5-[[(1,1'-Biphenyl)-4-yl]methoxy]-2-(4-morpholinyl)-3-oxocyclopentyl]-5-heptenoate, compound with ethyl acetate (10:1)

DMSO (0.61 ml) in $CH_2Cl_2$ (14 ml) was added dropwise to a stirred solution of acetyl bromide (0.57 ml) in $CH_2Cl_2$ (7 ml) under dry nitrogen at $-78°$. After 10 min. a solution of Intermediate 39 (1.05 g) in $CH_2Cl_4$ (14 ml) was added and stirring continued for 45 min. Triethylamine (2.87 ml) in $CH_2Cl_2$ (14 ml) was added at $-78°$ and the mixture was stirred at ambient temperature for 45 min. The mixture was poured into water (100 ml) and extracted with $CH_2Cl_2$ (3×30 ml). The combined extracts were dried and evaporated and the residue was purified by chromatography (E) to give the title compound as a solid (0.73 g), m.p. 45°–47°.

Analysis Found: C, 72.9; H, 7.0; N, 4.5; $C_{37}H_{42}N_2.O_6.O.1C_4H_8O_2$ requires: C, 72.5; H, 7.0; N, 4.5%.

EXAMPLE 23

[1α(Z),2β,5α]-(±)-(Acetyloxy)methyl 7-[5-[[(1,1'-Biphenyl)-4-yl]methoxy]-2-(4-morpholinyl)-3-oxocyclopentyl]-5-heptenoate A solution of Intermediate 30 (0.4 g), triethylamine (0.23 ml) and bromomethyl acetate (0.19 g) in dry acetone (6 ml) was stirred at 20° for 2 h then poured into pH 6.5 phosphate buffer (20 ml) and extracted with EA (2×20 ml). The combined extracts were dried and evaporated, and the residue was purified by chromatography (K) to give the title compound as an oil (0.3 g). I.R. ($CHBr_3$) 1755, 1740 cm$^{-1}$ Analysis Found: C, 69.7; H, 7.05; N, 2.3; $C_{32}H_{39}NO_7$ requires: C, 69.9; H, 7.15; N, 2.55%.

EXAMPLE 24

[1α(Z),2β,5α]-(±)-(3-Pyridinyl) 7-[5-[[(1,1'-Biphenyl)-4-yl]methoxy]-2-(4-morpholinyl)-3-oxocyclopentyl]-5-heptenoate A solution of Intermediate 30 (0.35 g) and triethylamine (0.41 ml) in acetone (7.5 ml) at $-10°$ was treated with iso-butylchloroformate (0.29 ml) and 0.25 h later with 3-hydroxypyridine (0.35 g). After 0.75 h, the solvent was removed in vacuo and the residue in pH 6.5 phosphate buffer (30 ml) was extracted with EA (3×25 ml). The combined extracts were washed with 0.2 N NaOH (30 ml), dried and evaporated, and the residue was purified by chromatography (II) to give the title compound as a solid (0.37 g), m.p. 74°–75°.

Analysis Found: C, 73.5; H, 6.9; N, 5.0; $C_{34}H_{38}N_2O_5$ requires: C, 73.6; H, 6.9; N, 5.1%.

EXAMPLE 25

[1α(Z),2β,5α]-(±)-[4-Aminocarbonyl)phenyl] 7-[5-[[4'-Methoxy(1,1'-biphenyl)-4-yl]methoxy]2-(4-morpholinyl)-3-oxocyclopentyl]-5-heptenoate A well stirred solution of Intermediate 43 (0.395 g) in DMSO (5 ml) and triethylamine (0.7 ml) was treated with pyridine-sulphur trioxide complex (0.3 g) in DMSO (5 ml) and was kept at 20° for 2 h. The mixture was poured into pH 6.5 phosphate buffer and extracted with $CH_2Cl_2$. The combined extracts were dried and evaporated, and the residue was purified by chromatography C through to B) to give the title compound as an oil (0.335 g). I.R. ($CHBr_3$) 3520, 3400, 1753(sh.), 1745, 1680 cm$^{-1}$ Analysis Found: C, 70.6; H, 7.0 N, 4.8; $C_{37}H_{42}N_2O_7$ requires: C, 70.9; H, 6.75; N, 4.5%.

EXAMPLE 26

[1α(Z),2β,5α]-(±)-(Acetylthio)methyl 7-[5-[[(1,1'-Biphenyl)-4-yl]methoxy]-2-(4-morpholinyl)-3-oxocyclopentyl]-5-heptenoate A well stirred solution of Intermediate 44 (0.31 g) in DMSO (4 ml) and triethylamine (0.6 ml) was treated with pyridine-sulphur trioxide complex (0.26 g) in DMSO (3 ml) and was kept at 20° for 1.5 h. The mixture was poured into EA (175 ml) and was washed with pH 6.5 phosphate buffer (3×30 ml) and brine (30 ml), then dried and evaporated. The residue was chromatographed twice (T then JJ) to give the pure title compound as an oil (0.2 g). I.R. ($CHBr_3$) 1740, 1700 cm$^{-1}$. T.L.C. (KK) $R_f$ 0.27

PHARMACEUTICAL EXAMPLES

Tablets

These may be prepared by direct compression or wet granulation. The direct compression method is preferred but may not be suitable in all cases as it is dependent upon the dose level and physical characteristics of the active ingredient.

| A. | Direct Compression | mg/tablet |
| --- | --- | --- |
| | Active ingredient | 100.00 |
| | Microcrystalline Cellulose B.P.C. | 298.00 |
| | Magnesium Stearate | 2.00 |
| | Compression Weight | 400.00 mg |

The active ingredient is sieved through a 250 m$^{-6}$ sieve, blended with the excipients and compressed using 10.0 mm punches. Tablets of other strengths may be prepared by altering the compression weight and using punches to suit.

| B. | Wet Granulation | mg/tablet |
| --- | --- | --- |
| | Active ingredient | 100.00 |
| | Lactose B.P. | 238.00 |
| | Starch B.P. | 40.00 |
| | Pregelatinised Maize Starch B.P. | 20.00 |
| | Magnesium Stearate B.P. | 2.00 |
| | Compressed Weight | 400.00 mg |

The active ingredient is sieved through a 250 m$^{-6}$ sieve and blended with the lactose, starch and pregelatinised starch. The mixed powders are moistened with purified water, granules are made, dried, screened and blended with the magnesium stearate. The lubricated granules are compressed into tablets as described for the direct compression formulae. The tablets may be film coated with suitable film forming materials, e.g. methyl cellulose or hydroxylpropyl methyl cellulose using standard techniques. Alternatively the tablets may be sugar coated.

| Capsules | mg/capsule |
| --- | --- |
| Active ingredient | 100.00 |
| *STA-RX 1500 | 99.00 |
| Magnesium Stearate B.P. | 1.00 |

| Capsules | mg/capsule |
|---|---|
| Fill Weight | 200.00 mg |

*A form of directly compressible starch supplied by Colorcorn Ltd., Orpington, Kent.

The active ingredient is sieved through a 250 m$^{-6}$ sieve and blended with the other materials. The mix is filled into No. 2 hard gelatin capsules using a suitable filling machine. Other doses may be prepared by altering the fill weight and if necessary changing the capsule size to suit.

| Inhalation Cartridges | /cartridge |
|---|---|
| Active ingredient (micronised) | 3 mg |
| Lactose B.P. to | 25 mg |

The active ingredient is micronised so that the majority of the particles are between 1 m$^{-6}$ and 5 m$^{-6}$ in longest dimensions and none are greater than 10 m$^{-6}$. The active ingredient is then blended with the lactose and the mix is filled into No. 3 hard gelatin capsules using a suitable filling machine.

| Suspensions | mg/5 ml dose |
|---|---|
| Active ingredient | 100.0 |
| Aluminium monostearate | 75.0 |
| Sucrose (powdered) | 125.0 |
| Flavour | as required |
| Colour | |
| Fractionated coconut oil to | 5.00 ml. |

The aluminium monostearate is dispersed in about 90% of the fractionated coconut oil. The resulting suspension is heated to 115° C. while stirring and then cooled. The flavour and colour are added and the active ingredient and sucrose are suitably dispersed. The suspension is made up to volume with the remaining fractionated coconut oil and mixed.

| Injection for Intravenous Administration | |
|---|---|
| Active ingredient | 50 mg |
| Suitable vehicle to | 5 ml. |

A sterile presentation of the active ingredient in an ampoule or vial together with an ampoule containing a suitable vehicle. The former may be prepared by (a) filling sterile material into vials under aseptic conditions (b) freeze drying a sterile solution of the active ingredient under aseptic conditions.

The vehicle may be (a) Water for Injections B.P. (b) Water for Injections B.P. containing: (1) sodium chloride to adjust the tonicity of the solution and/or (2) buffer salts or dilute acid or alkali to facilitate solution of the active ingredient.

The vehicle is prepared, clarified and filled into appropriate sized ampoules sealed by fusion of the glass. The vehicle is sterilised by heating in an autoclave using one of the acceptable cycles.

We claim:

1. Compounds of the general formula (1)

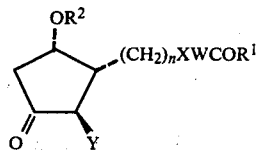

wherein $R^1$ is (a) —$AR^3$ where A is —O— or —S— and $R^3$ is phenyl [optionally substituted by $C_{1-4}$ alkyl, $C_{1-4}$ alkoxy, $C_{1-4}$ alkanoyl, methylthio, methylsulphinyl, methylsulphonyl, halogen, —$CO_2R^4$ [where $R^4$ is a hydrogen atom, $C_{1-4}$ alkyl or phenyl], —$NHCOR^4$, —$CONR^5R^6$ [where $R^5$ and $R^6$ may be the same or different and are each a hydrogen atom or $C_{1-4}$ alkyl], $C_{1-4}$ alkylsulphonylamino, formyl, nitro, cyano, phenyl or —$NR^5R^6$];

(b) —$OCH_2COR^7$ where $R^7$ is phenyl (optionally substituted by a halogen atom, $C_{1-4}$ alkyl or $C_{1-4}$ alkoxy) or —$NH_2$;

(c) —$A(CH_2)_mBR^5$ where m is 1-3 and B is —O— or —S—, provided that when m is 1, $R^5$ is not a hydrogen atom;

(d) —$A(CH_2)_pR^8$ where p is 2 or 3 and $R^8$ is an N-attached $C_{1-4}$ dialkylamino, morpholino, piperidino, pyrrolidino, acetylamino or benzoylamino group;

(e) —$OCH(CH_2N(CH_3)_2)_2$ (f)

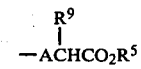

where $R^9$ is a hydrogen atom, methyl or phenyl;

(g) —$OCH_2OCOR^{10}$ where $R^{10}$ is $C_{1-4}$ alkyl, methoxy or phenyl;

(h) —$OCH_2SCOR^{11}$ is $C_{1-4}$ alkyl;

(i) pyridinyloxy or pyridinylthio;

(j) 1-(acetyloxy)ethoxy, (acetyloxy)phenylmethoxy, tetrahydro-5-oxo-2-furanyloxy, tetrahydro-2-oxo-3-furanyloxy, triphenylmethoxy or diphenylmethoxy; or (k) —$OR^{12}$ where $R^{12}$ is $C_{3-6}$ alkenyl, $C_{5-7}$ cycloalkyl (optionally substituted by one or more $C_{1-4}$ alkyl groups), —$CH_2CCl_3$ or furanylmethyl;

n is 1 or 2;

W is straight or branched $C_{1-7}$ alkylene;

X is cis or trans —CH=CH— or —$CH_2CH_2$—;

Y is a saturated heterocyclic amino group (attached to the cyclopentane ring via the nitrogen atom) which has 5-8 ring members and (a) optionally contains in the ring —O—, —S—, —$SO_2$—, or $NR^{13}$ (where $R^{13}$ is a hydrogen atom, $C_{1-7}$ alkyl or aralkyl having a $C_{1-4}$ alkyl portion); and (b) is optionally substituted by one or more $C_{1-4}$ alkyl groups;

$R^2$ is (i) straight or branched $C_{1-5}$ alkyl substituted by (a) phenyl [optionally substituted by $C_{1-6}$ alkyl, $C_{5-7}$ cycloalkyl, phenylalkyl having a $C_{1-3}$ alkyl portion, thienyl, phenyl (optionally substituted by $C_{1-4}$ alkyl, $C_{1-4}$ alkoxy or phenyl), benzoyl (optionally substituted by $C_{1-4}$ alkyl, $C_{1-4}$ alkoxy, halogen, trifluoromethyl or phenyl) or $C_{5-7}$ cycloalkanoyl], (b) thienyl [optionally substituted by $C_{5-7}$ cycloalkyl or phenyl (optionally substituted by $C_{1-3}$ alkyl, $C_{1-3}$ alkoxy or halogen)], or (c) naphthyl (optionally substituted by $C_{1-4}$ alkyl or $C_{1-4}$ alkoxy), or (ii) cinnamyl (optionally substituted by benzoyl); and the physiologically acceptable salts and solvates thereof.

2. Compounds as claimed in claim 1 in which Y is morpholino or piperidino.

3. Compounds as claimed in claim 1 in which X is cis —CH=CH—.

4. Compounds as claimed in claim 1 in which n is 2 and W is —CH$_2$CH$_2$— or CH$_2$CH$_2$CH$_2$CH$_2$—.

5. Compounds as claimed in claim 1 in which R$^2$ is a benzyl group in which the phenyl group is substituted by thienyl or phenyl, which latter phenyl is optionally substituted by $C_{1-4}$ alkyl or $C_{1-4}$ alkoxy.

6. Compounds as claimed in claim 1 in which R$^1$ is —OCH$_2$OCOCH$_3$, —OCH$_2$SCH$_3$, —O(CH$_2$)$_3$NHCOCH$_3$, —OCH$_2$CONH$_2$, 4-acetamidophenoxy or allyloxy.

7. Compounds as claimed in claim 1 in which:
R$^1$ is —OCH$_2$OCOCH$_3$, —OCH$_2$SCH$_3$, —O(CH$_2$)$_3$NHCOCH$_3$, —OCH$_2$CONH$_2$, 4-acetamidophenoxy or allyloxy,
W is —CH$_2$CH$_2$—,
n is 2,
X is cis —CH=CH—
Y is morpholino or piperidino and
R$^2$ is benzyl in which the phenyl group is substituted by phenyl, tolyl or methoxyphenyl,
and the physiologically acceptable salts and solvates thereof.

8. Compounds as claimed in claim 1 in which the carbon atom carrying the —(CH$_2$)$_n$XWCOR$^1$ group is in the R- configuration 9. A pharmaceutical composition comprising a compound as claimed in claim 1 and one or more pharmaceutical carriers.

* * * * *